United States Patent
Cormier

(10) Patent No.: US 10,156,551 B2
(45) Date of Patent: *Dec. 18, 2018

(54) SAMPLING SYSTEMS AND METHODS OF USING THE SAME

(71) Applicant: Waters Technologies Corporation, Milford, MA (US)

(72) Inventor: Sylvain Cormier, Mendon, MA (US)

(73) Assignee: WATERS TECHNOLOGIES CORPORATION, Milford, MA (US)

(*) Notice: Subject to any disclaimer, the term of this patent is extended or adjusted under 35 U.S.C. 154(b) by 363 days.

This patent is subject to a terminal disclaimer.

(21) Appl. No.: 14/850,366

(22) Filed: Sep. 10, 2015

(65) Prior Publication Data

US 2016/0077061 A1 Mar. 17, 2016

Related U.S. Application Data

(60) Provisional application No. 62/049,766, filed on Sep. 12, 2014.

(51) Int. Cl.
*G01N 30/04* (2006.01)
*G01N 30/20* (2006.01)
*G01N 30/24* (2006.01)

(52) U.S. Cl.
CPC ............. *G01N 30/20* (2013.01); *G01N 30/24* (2013.01); *G01N 2030/202* (2013.01)

(58) Field of Classification Search
CPC ........ G01N 30/20; G01N 30/24; G01N 30/12; G01N 2030/202; G01N 2030/025;
(Continued)

(56) References Cited

U.S. PATENT DOCUMENTS 7,661,301 B2 * 2/2010 Moor ..................... G01N 21/68
  73/149
8,343,774 B2 * 1/2013 Cormier ................ G01N 30/16
  210/198.2

(Continued)

OTHER PUBLICATIONS

T. Jiang Y., Vaidya L., The Waters ACQUITY Ultra-Performance Liquid Chromatograph and the Micromass Quattro Premier Triple Quadrupole Mass Spectrometer, Dec. 2012.

*Primary Examiner* — Harshad R Patel
*Assistant Examiner* — Nigel Plumb
(74) *Attorney, Agent, or Firm* — Schmeiser, Olsen & Watts LLP

(57) ABSTRACT

A sampling system comprising an external sampling assembly in fluidic communication with a process sample manager is provided herein. The sampling system can automatically acquire sample from one or more sources of sample to prepare sample for injection into a column or detector. The external sampling assembly has an external sampling valve connected to an external pump and is in fluidic communication with a process sample manager. The external sampling valve has a first configuration and a second configuration useful in three steps of drawing, loading and discharging sample. Two selection valves can be connected to a plurality of external sampling valves for sequential sampling of multiple sources of sample. Sample can also be diluted in the process sample manager and then combined in a solvent composition stream for injection into the column or the detector.

20 Claims, 18 Drawing Sheets

(58) Field of Classification Search
CPC .. G01N 33/006; G01N 33/2847; G01N 33/18; G01N 7/14
USPC .......... 73/61.55, 61.59, 61.52, 61.43, 64.41, 73/53.01, 23.41, 23.42, 19.1, 23.35
See application file for complete search history.

(56) References Cited

U.S. PATENT DOCUMENTS

| | | | |
|---|---|---|---|
| 2011/0016955 A1* | 1/2011 | Cormier | G01N 1/38 73/61.55 |
| 2011/0202188 A1* | 8/2011 | Pensak, Jr. | G01N 35/1097 700/285 |
| 2012/0103075 A1* | 5/2012 | Cormier | F04B 13/02 73/61.55 |
| 2012/0303167 A1* | 11/2012 | Heden | G01N 30/24 700/282 |
| 2012/0305464 A1* | 12/2012 | Cormier | G01N 30/20 210/198.2 |
| 2016/0195564 A1* | 7/2016 | Hewitson | G01N 30/06 436/54 |

\* cited by examiner

SAMPLING SYSTEMS AND METHODS OF USING THE SAME

CROSS REFERENCE TO RELATED APPLICATIONS

This application claims the benefit of priority to the U.S. Provisional Application No. 62/049,766 filed Sep. 12, 2014 incorporated herein by reference.

BACKGROUND OF THE INVENTION

Various industries use liquid chromatography systems to analyze and control bioprocess and chemical reactions. For example, pharmaceutical manufacturers often use a liquid chromatography system to monitor their process line by taking samples at various times or at different points along the process line to ensure that the batch or process flow stream is to specification. Samples taken may include, but are not limited to, complex mixtures of proteins, protein precursors, protein fragments, reaction products, and other compounds, to list but a few. Other manufacturers may use liquid chromatography systems to profile a certain biochemical reaction, taking samples from the same point in the process line over time as the reaction progresses.

The manner of acquiring samples for analysis can be manually intensive, especially where there are multiple reactors and different types of processes involved. An individual must typically draw the sample manually from a process line, carry it to the liquid chromatography system, and load it into the system for injection and analysis. Throughout this handling, care must be taken to label the sample properly and to ensure a well-documented chain of custody, or otherwise risk introducing uncertainty into the results. In addition, if the sample requires dilution before injection to the column or detector, the individual must first thoroughly wash the container within which the dilution occurs to avoid contamination with previously sampling. Moreover, manually prepared sample dilutions are often wasteful and not cost effective.

As a result, monitoring multiple bioprocess and chemical processes in a timely manner (preferably in-line or on-line) tenders in an increased level of efficiency in testing while at the same time reducing over-processing, enhancing consistency and minimizing rejects.

SUMMARY OF THE INVENTION

A sampling system configured to automatically acquire sample from at least one non-pressurized source of sample can have an external sampling assembly in fluidic communication with the at least one source of sample and a process sample manager connected to the external sampling assembly. In one aspect, the external sampling assembly can have an external sampling valve having a first sample loop and an external pump. In exemplary embodiments, the process sample manager is in fluidic communication with a column or a detector and has an online sampling valve connected to the external sampling valve. The external sampling valve can have a first configuration and a second configuration. For example, in the first configuration, the external sampling valve can be configured to place the process sample manager in fluidic communication with the first sample loop. In a second configuration, the external sampling valve can be configured to place the external pump in fluidic communication with the first sample loop. The process sample manager can also be in fluidic communication with a solvent delivery system.

Further, the process sample manager can have a priming valve and a fluidic tee where the priming valve can be connected to the online sampling valve and the fluidic tee. The process sample manager can also have a diluent source and a diluent pump. For example, the diluent pump and the diluent source can be connected to the priming valve and the diluent pump is in fluidic communication with the diluent source or the fluidic tee. Also, the process sample manager can have a process valve connected to a first wash reservoir and a process pump. For example, the process pump is configured to be in fluidic communication with the external sampling assembly or the first wash reservoir, and the process valve can be configured to discharge wash to the external sampling valve.

In another aspect, a sampling system can be configured to acquire sample from a plurality of non-pressurized sources of sample and can discharge or inject sample into a column or detector. The external sampling assembly can have a plurality of external sampling valves, at least two selection valves and an external pump. For example, each of the external sampling valves can have a first sample loop. In the first configuration, the first sample loop of the external sampling valve can be in fluidic communication with the at least two selection valves. Also, each of the at least two selection valves can be connected to the process sample manager. Further, the online sampling valve can be connected to each selection valve.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Figure 1:
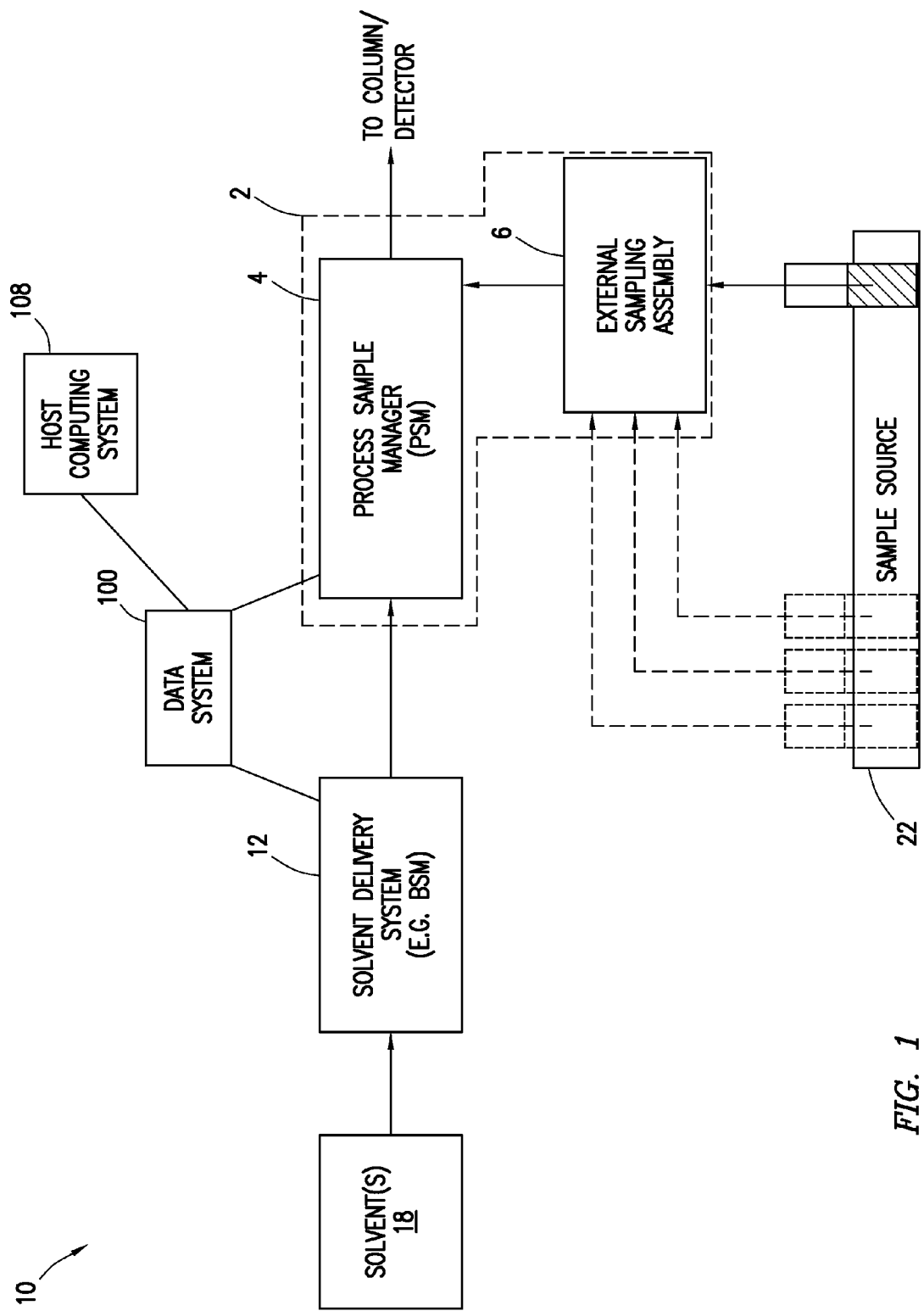
FIG. 1 is a block diagram showing a liquid chromatography system utilizing the sampling system presented herein.

As used herein, "online" means that the sample manager is connected directly to a process (or production) line to acquire samples from the process line in approximately real time without manual intervention, then load, and inject the acquired process samples for subsequent chromatographic analysis. The chromatographic analysis thus occurs in parallel to the continued operation of the process line. No distinction is made here between a production line and a process line.

An "at-line" system means that the system is physically near but unconnected to the process line from which an individual acquires a process sample manually, carries and places the process sample into the system for processing.

An "in-line" system is one that is physically incorporated within the process line (i.e., the chromatographic analysis and process line operations in this instance are akin to serial processing).

Advantageously, the online system described herein does not require a separate container within which to perform the dilution. Rather, the dilution can occur within the plumbing (i.e., tubing and other internal components) of the sample manager by merging the acquired process sample with a diluent stream. Hence, a separate container is not required and does not need to be washed to avoid contamination with a previously acquired and diluted sample. As another advantage, the online system uses smaller amounts of sample than dilution executed in a container. In addition, the sampling system described herein can reduce the amount of sample consumed by a process sample manager and allows for multiple connections to reactors and other vessels without disturbing or disrupting the processes. Hence, the process sample manager can sample concentrated reactions and larger dilution ranges. Preferably, sample dilution ranges from about 1 to 99 units of diluent to 1 unit of sample. However, the dilution range of a sample can extend to 5000 to 1. The sampling system described herein also permits quenching of the sample. Furthermore, the undiluted sample does not contact the pumps which increases pump life due to the lack of harsh conditions.

Additionally, the sampling system can be configured to be a trace enrichment device. To operate as a trace enrichment device, sample is drawn from the reactor or reactor flow stream into the external sampling valve comprising a trap column. The trap column removes unwanted molecules, macromolecules and other components and impurities from the sample. Also, the sampling system described herein can be configured to be an on-line injector, bypassing the process sample manager or simply by connecting the external sampling valve(s) directly to an HPLC/UPLC pump and a column or detector. In addition, as described herein, the external sampling assembly can work as a trace enrichment device by interchanging the sample loop with a trap column.

Generally, the process sample manager (sometimes referred to herein as "PSM") is useful in both manufacturing and research environments. Process sample managers automatically manage sample aspiration and injection, collection and fraction analysis on a single platform and can be designed for use with HPLC or LC/MS systems. As described herein, an external pump assembly directly connects to reactor or process line to acquire the sample automatically in real time without manual intervention. However, the external pump assembly can also work with human intervention, manually. Furthermore, because the assembly and/or the process sample manager can work off-line, samples can be quenched, diluted and/or injected into chromatography equipment on demand. Multiple analyses can occur in parallel and during operation of various processes.

FIG. 1 is a block diagram of a liquid chromatography system 10 for separating a mixture into its constituents as provided herein. The liquid chromatography system 10 includes a sampling system 2 and a solvent delivery system 12. The sampling system 2 is in fluidic communication with one or more sources of sample such as a reactor or a reactor flow stream. The sampling system 2 is also in fluidic communication with a solvent delivery system 12. The solvent delivery system 12 provides a solvent composition stream to the sampling system 2 via the process sample manager 4. Subsequently, the solvent composition stream is combined with diluted sample and sent to, and received by, a chromatographic column or detector (not shown). The sampling system 2 comprises a process sample manager 4 and an external sampling assembly 6. The sampling system 2 by way of the external sampling assembly 6 is directly connected to the reactor 22 or other source of sample such as a vessel, reactor flow stream or process line by tubing. The sampling system 2 can automatically or manually acquire samples from a reactor 22 or a reactor flow stream (not shown).

The external sampling assembly 6 can acquire a sample from one or more points on the process flow stream, the reactor flow stream or directly from the reactor or from multiple sources of sample. The external sampling assembly 6 may acquire samples at different stages (location and/or time-based) of the manufacturing process from one or more reactors or processes. For example, the external sampling assembly 6 can acquire samples from the reactor or reactor flow stream at different time intervals in order to monitor the progress of a chemical reaction. Furthermore, the external sampling assembly 6 can acquire samples continuously or at different stages (location and/or time-based). In general, the reactor 22 or other vessel and/or the reactor flow stream or other process lines are representative of sample sources including manufacturing processes, beaker reactions, exit line (cleaning validation), reaction chamber and fermentation reactions.

As noted above and shown in the figures, the external sampling assembly 6 can be used as a trace enrichment device if the first sample loop 62 is replaced with a trap column 80. Trap columns are typically short columns that can be used to remove a variety of unwanted components, impurities and other contaminants including but not limited to organic contaminants, cations, anions, metals and other types of chemical and biological compounds. Trap columns are typically packed columns with high-capacity ion exchange (cation or anion) resins but other types of trap columns may also be useful. A specific exemplary trap column is the nanoACQUITY UPLC 2G trap column manufactured by Waters Corporation. Also, the external sampling assembly 6 can be an on-line injector where the external sampling valve 24 is connected directly to the solvent delivery system 12 and the column (HPLC/UPLC) 86 or column heater (not shown).

Importantly, the external sampling assembly 6 allows the process sample manager 4 to monitor any one or more processes or reactors which may be located a substantial distance from the process sample manager 4, or, alternatively, in close proximity to the process sample manager 4. As such, the term "remote" as used herein simply means separate (i.e., a separate module) or detached. The term remote is not intended to mean that the external sampling valve assembly 6 is isolated from or otherwise positioned or located a significant distance away from process sample manager 4 and/or the source of sample including the reactor 22 or reactor flow stream. Hence, the devices and methods described herein may include those situations where the external sampling assembly 6 is close or positioned next to or even within the process sample manager 4 or a substantial distance apart.

As shown in FIG. 1, the process sample manager 4 is in fluidic communication with the external sampling assembly 6 which is in fluidic communication with a reactor 22 or reactor flow stream. The external sampling assembly 6 is also in fluidic communication with the process sample manager 4. The process sample manager 4 is in fluidic communication with a diluent source 68 and the solvent delivery system 12. Moreover, the process sample manager 4 is in fluidic communication with a chromatographic column 86 of particulate matter or a detector such as a mass spectrometer, for receiving an elution comprised of a diluted process sample combined with the solvent composition stream provided by the solvent delivery system 12. A mass spectrometer can be used in connection with the subject systems and methods.

The solvent delivery system 12 (not shown in detail) typically includes a low-pressure gradient pumping system (not shown) in fluidic communication with reservoirs 18 from which the pumping system draws liquid solvents through tubing. In a low-pressure gradient pumping system, the mixing of solvents typically occurs before the pump (not shown). The solvent delivery system 12 also may have a mixer (not shown) in fluidic communication with the solvent reservoirs 18 to receive various solvents in metered proportions. This mixing of solvents occurs in accordance with an intake profile, and produces a solvent (mobile phase) composition that remains unchanged (isocratic) or varies over time (gradient). Hence, the pumping system of a solvent delivery system 12 is in fluidic communication with a mixer and can draw a continuous flow of solvent mixture therefrom for delivery to an autosampler such as the process sample manager 4. To draw and deliver the solvent mixture, the pumping system (not shown) can provide a flow rate in the range of 0.010 ml/min to 2 ml/min at 15,000 psi. Examples of systems that can be used include, but are not limited to, the ACQUITY HPLC Binary Solvent Manager, manufactured by Waters Corp. of Milford, Mass. See, U.S. 2012/0303167 at ¶[0019].

By way of example, the solvent delivery system 12 can be a binary solvent manager ("BSM"), which uses two individual serial flow pumps to draw solvents from a reservoir 18 and deliver the solvent composition to the PSM 4. Here, each of the BSM's two independent pumps contains two linear-drive actuators. Each actuator pair comprises a single reciprocating serial pump that delivers precise flow of a single solvent. The two pump systems combine their two solvents at a filter/tee mixer. From there, the solvent mixture flows into the process sample manager 4. A gradient elution program is commonly used so that the eluent composition (and strength) is steadily changed during the analysis. This increases separation efficiency, decreases the retention time and improves peak shape by minimizing tailing. T Jiang Y, Vaidya L, *The Waters ACQUITY® Ultra-Performance Liquid Chromatograph and the Micromass Quattro Premier Triple Quadrupole Mass Spectrometer*, December, 2012.

The liquid chromatography system 10 may also include a data system 100 that is in signal communication with the sampling system 2 and the solvent delivery system 12. The data system 100 has a processor (not shown) and a switch (not shown), e.g., an Ethernet switch for handling signal communication between the solvent delivery system 12 and the sampling system 2. In addition, the data system 100 is programmed to implement the various phases of operation performed by the sampling system 2 (e.g., turning pumps on and off, rotating valves) in order to automatically acquire and dilute a process sample and introduce the diluted process sample to the solvent composition stream, as described herein. In addition, a host computing system 108 is in communication with the data system 100, by which personnel can download various parameters and profiles to affect the data system's performance.

Each of the valves described herein is a separate, independently operable rotary valve having a plurality of fluidic ports and one or more flow-through conduits. Although described primarily as rotary valves, any one or more of these valves: priming, sampling, selection, and/or injection, can be other types of valve including, but not limited to, slider valves, solenoids, and pin valves. Each flow-through conduit provides a pathway between a pair of neighboring fluidic ports. When a given valve rotates, its flow-through conduits move clockwise or counterclockwise, depending upon the valve's direction of rotation. This movement operates to switch the flow-through conduit to a different pair of neighboring fluidic ports, establishing a fluidic pathway between that different pair while removing the pathway from the previously connected pair of fluidic ports.

In addition, as described herein and unless otherwise specified, all connections are fluidic and provide for fluid flow, including but not limited to, tubing connections between fluidic ports and devices such as the reactor, the reactor flow stream, valves, pumps and other apparatus such as injection needles, tees, and reservoirs that are described herein. Such connections are typically made via tubing ranging in size from 0.005 to 0.150 inches and can be made of stainless steel, PEEK, Teflon and/or any material suitable for the pressure and composition of the sample. Also, flow-through conduits are fluidical connections where the ports and conduits are fluidically connected to each other and/or other devices described. Hence, when it is stated that a device, fluidic port or flow-through conduit is connected or in fluidic communication with the other, this means and should be understood to mean that such connection is fluidic unless otherwise noted.

As shown in the figures, the sampling system 2 comprises the process sample manager 4 and the external sampling assembly 6. As noted above, the external sampling assembly 6 comprises at least one external pump 28, at least one external sampling valve 24, and optionally, a plurality of selection valves 26. The process sample manager 4 comprises the priming valve 32, the online sampling valve 34, the process valve 36, and the injection valve 38. The process sample manager 4 further includes a diluent pump 40, a sample pump 42, a process pump 44, an injection needle 58 and a fluidic tee 46.

The External Sampling Assembly

Figure 2A:
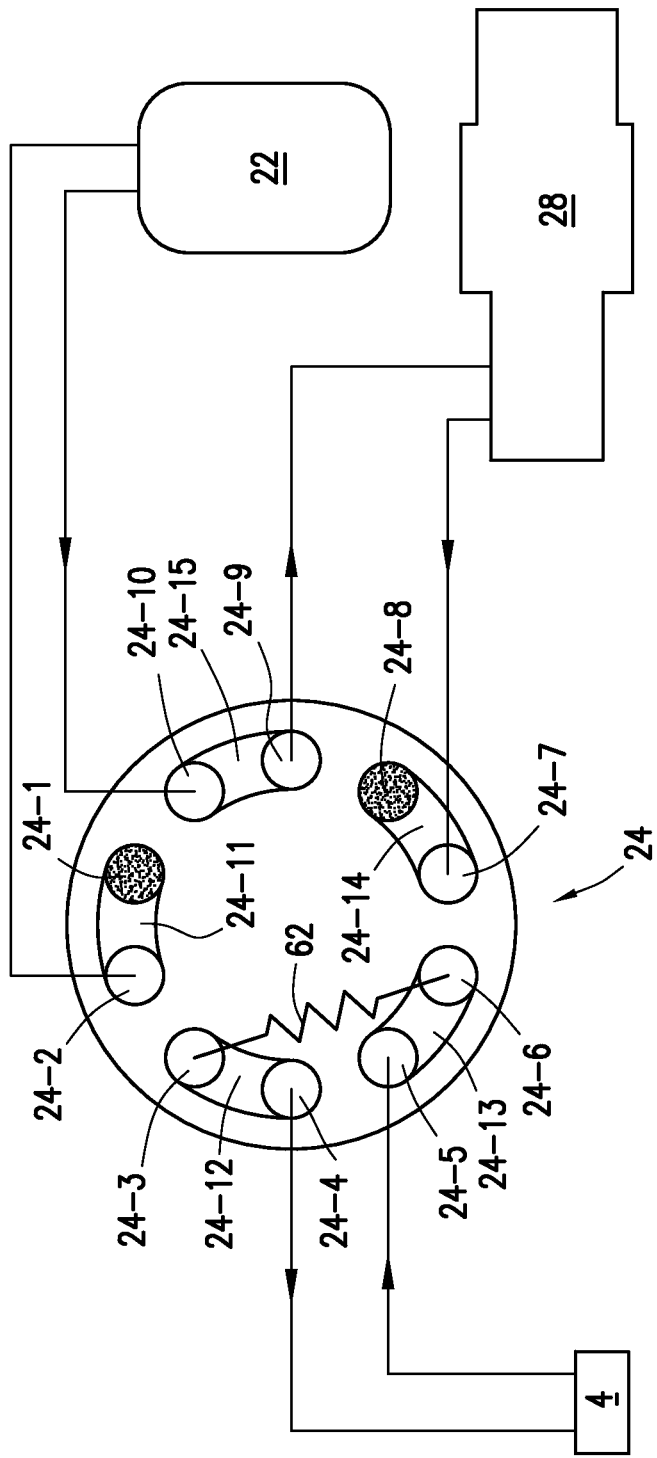
FIG. 2A shows the external sampling assembly configured to draw sample from the reactor into the external sampling valve and discharge drawn sample to the process sample manager.
Figure 2B:
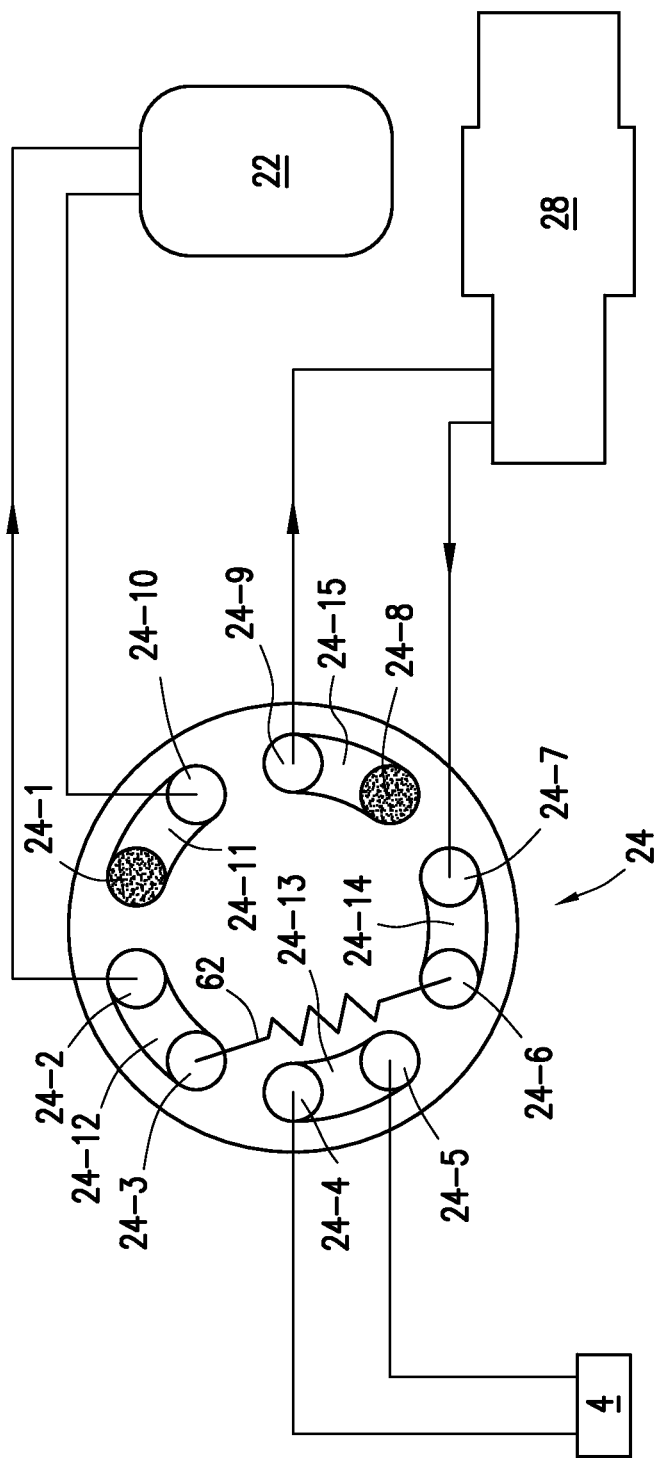
FIG. 2B shows the external sampling assembly configured to displace drawn sample from the first sample loop of the external sampling valve and recirculate it back to the reactor.
Figure 3:
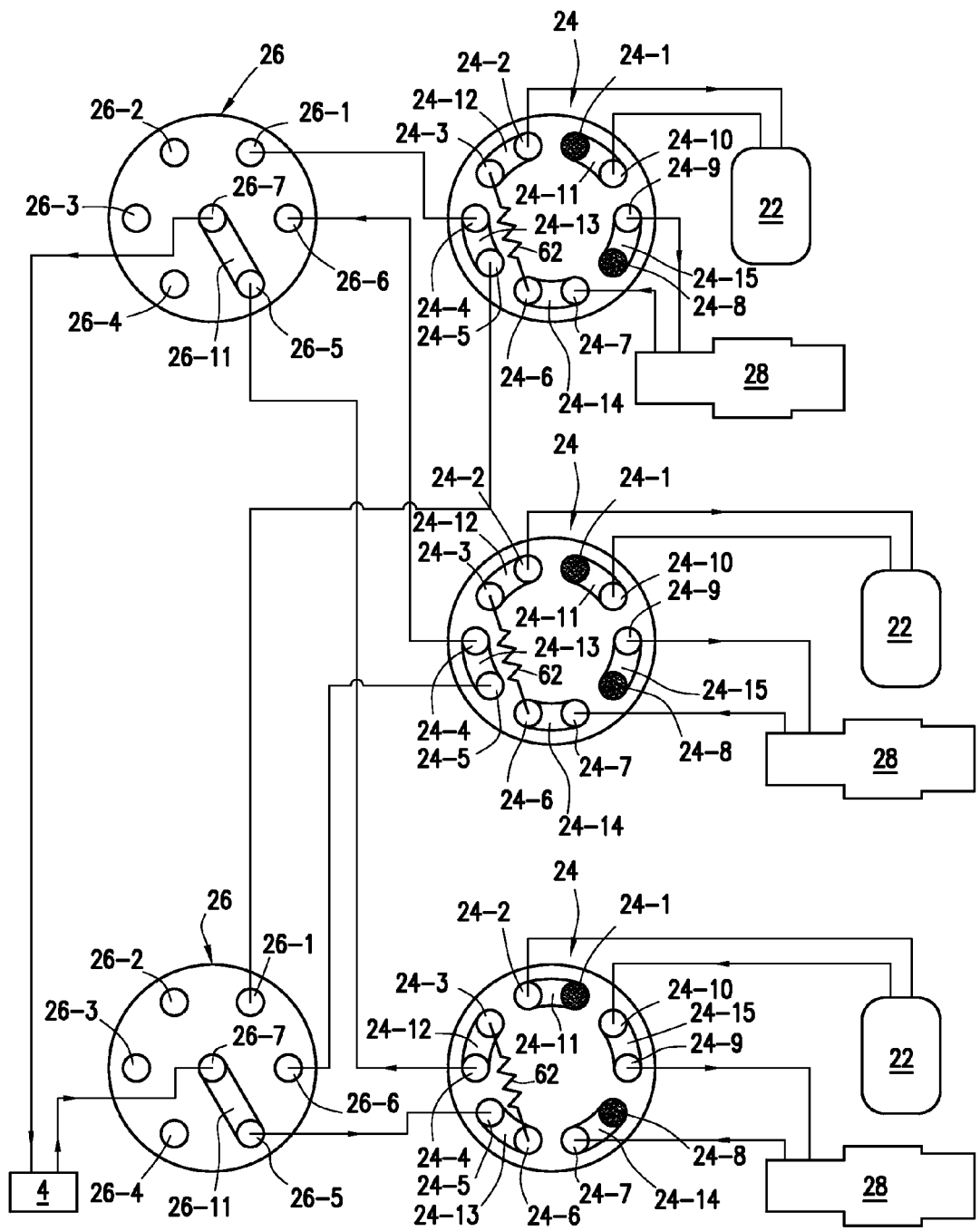
FIG. 3 shows the external sampling assembly configured to draw sample from multiple reactors and including a plurality of external sample valves, a plurality of external pumps and one or more selection valves.

As shown in FIGS. 2A and 2B and FIG. 3, the external sampling assembly 6 includes one or more external sampling valves 24 and one or more external pumps 28 combined in a way that allows sampling from one or more non-pressurized supply of sample such as a reactor 22 or reactor stream 22 or dissolution bath (not shown). The external sampling assembly 6 can be used to draw a plurality of process samples from a single source of sample or, with the use of a selection valve 26, a plurality (more than one) of reactors 22 or dissolution baths or other sources of sample.

As shown in the figures, the external sampling valve 24 has ten fluidic ports 24-1, 24-2, 24-3, 24-4, 24-5, 24-6, 24-7, 24-8, 24-9, and 24-10 and five flow-through conduits 24-11, 24-12, 24-13, 24-14, and 24-15. Fluidic ports 24-1 and 24-8 are plugged and not used for fluid flow of sample. A first sample loop 62 connects fluidic ports 24-3 and 24-6. Tubing connects the external sampling valve 24 to the reactor 22 and to the external pump 28. Tubing also connects the external sampling valve 24 to the process sample manager 4. More specifically, tubing connects fluidic port 24-2 and fluidic port 24-10 to the reactor 22. Tubing further connects fluidic ports 24-7 and 24-9 to the external pump 28. In addition, tubing connects the fluidic port 24-4 to the fluidic port 34-5 of the online sampling valve 34 and fluidic port 24-5 to the fluidic port 36-3 of the process valve 36.

The external pump 28 is a positive displacement pump. During startup, a liquid positive displacement pump cannot simply draw air until the feed line and pump fill with the liquid that requires pumping. Typically, an operator must introduce liquid into the system to initiate the pumping. While loss of prime is usually due to ingestion of air into the pump, the clearances and displacement ratios in pumps for liquids and other more viscous fluids usually cannot displace air due to its higher compressibility.

The selection valve 26 has seven fluidic ports 26-1, 26-2, 26-3, 26-4, 26-5, 26-6 and 26-7 and one flow-through conduit 26-11. The number of selection valves 26 depends, in part, on the number of external sampling valves 24. It is optional for the external sampling assembly 6 to include one or more selection valves 26 with only one external sampling valve 24. However, the external sampling assembly 6 comprising a plurality of external sampling valves 24 needs at least two or more selection valves 26. Further, whenever the selection valve 26 is included in the sampling system 2, there are at least two selection valves 26 in order that the process pump 44 can move sample through the external sampling valve 24 and in and out of the selection valves 26 to the process sample manager 4.

When samples are drawn from a plurality of reactors 22, there is at least one external sampling valve 24 in fluidic communication with each reactor 22. Furthermore, when the external sampling assembly 6 comprises two or more external sampling valves 24, at least two selection valves 26 are required. In other words, while a plurality of external sampling valves 24 and/or a plurality of selection valves 26 could be connected to a single reactor 22, at least two selection valves 26 must be provided for the external sampling assembly 6 having two or more external sampling valves 24. For the external sampling assembly 6 having a plurality of external sampling valves 24, tubing connects fluidic port 24-4 of each external sampling valve 24 to each selection valve 26. Likewise, fluidic port 24-5 of each external sampling valve 24 is connected with tubing to each selection valve 26. Fluidic ports 24-4 and 24-5 can be connected to any of fluidic ports 26-1, 26-2, 26-3, 26-4, 26-5 or 26-6 of the selection valve 26 and in alternative combinations.

More specifically, as shown in FIGS. 2A and 2B and FIG. 3, tubing connects fluidic ports 24-7 and 24-9 of the external sampling valve 24 to the external pump 28. Tubing connects fluidic ports 24-10 and 24-2 of the external sampling valve 24 to the reactor 22 or other source of sample. Tubing connects fluidic ports 24-4 and 24-5 of the external sampling valve 24 to fluidic port 34-5 of the online sampling valve 34 and fluidic port 36-3 of the process valve 36 of the process sample manager 4 when a single external sampling valve 24 is used (FIGS. 2A and 2B). Or, alternatively, for the external sampling assembly 6 having a plurality of external sampling valves 24, tubing connects fluidic port 24-4 and fluidic port 24-5, each to one of fluidic port 26-1, 26-2, 26-3, 26-4, 26-5 or 26-6 of the selection valve 26.

FIG. 3 depicts an example of the external sampling assembly 6 comprising three external sampling valves 24 and two selection valves 26. Tubing connects fluidic port 26-7 of each of the selection valves 26 to either the process valve 36 or the online sampling valve 34 of the process sample manager 4. Tubing also connects fluidic port 24-5 of each of the external sampling valves 24 to each of the selection valve 26 at fluidic ports 26-1, 26-5 and 26-6. As shown, fluidic port 26-7 of one of the selection valves 26 is connected to fluidic port 36-3 of the process valve 36 of the process sample manager 4. Fluidic port 26-7 of the other selection valve 26 is then connected to fluidic port 34-5 of the online sampling valve 34 of the process sample manager 4. Flow-through conduit 26-11 of each selection valve 26 connects fluidic ports 26-7 to fluidic ports 26-5.

The various combinations of valve configurations of the selection valve 26 and the external sampling valve 24 effectively determine the fluidic pathway from the reactor 22, the external sampling valve 24, and the selection valve 26 to the process sample manager 4. In short, the configuration of each selection valve 26 determines which fluidic pathway of sample from which reactor 22 will flow to the process sample manager 4. As also shown in FIG. 3, two of the three external sampling valves 24 are in the second configuration (FIG. 2B) and the other external sampling valve 24 is in the first configuration (FIG. 2A) as described above. Alternatively, each of the external sampling valves 24 can be in the first configuration, as shown in FIG. 2A. As another alternative, the selection valve 26 could have eight fluidic ports and one flow-through conduit (not shown). If an eight position selection valve 26 is used, then the sampling system described herein could have seven or eight external sampling valves 24.

Process Sample Manager

The process sample manager 4 comprises the priming valve 32, the online sampling valve 34, the process valve 36, and the injection valve 38. The process sample manager 4 further includes a diluent pump 40, a sample pump 42, an injection needle 58 and a fluidic tee 46.

The priming valve 32 has six fluidic ports 32-1, 32-2, 32-3, 32-4, 32-5 and 32-6 and two flow-through conduits 32-11 and 32-12. Tubing connects fluidic port 32-1 to fluidic port 34-3 of the online sampling valve 34. Likewise, tubing connects fluidic port 32-2 to a diluent source 68. Further, tubing connects fluidic port 32-3 to the diluent pump 40. Tubing connects fluidic port 32-4 to the fluidic tee 46. Fluidic port 32-5 is connected to a second wash reservoir 51. Tubing connects fluidic port 32-6 to the sample pump 42. The two flow-through conduits 32-11 and 32-12 can move clockwise and counterclockwise for diluent to flow into the fluidic tee 46 and to push sample through to the injection needle 58.

The process sample manager 4 also includes the fluidic tee 46 having a seat 70 and a first inlet 72 to receive diluent from the priming valve 32. The fluidic tee 46 has a first outlet 76 connected to the injection valve 38. The fluidic tee 46 also has a second inlet 74 connected to a wash pump 48. During a wash cycle further described below, the wash pump 48 receives wash from a third wash reservoir 52 and pumps wash to the fluidic tee 46 through a second outlet 78 fluidically connected to a second waste reservoir 55. The use of fluidic tees is further described in U.S. Pat. No. 7,754,075 issued Jul. 13, 2010 at Col. 5, l. 8 to Col. 8, l. 18, incorporated herein by reference.

In operation, the tip of an injection needle 58 moves in and out of the seat 70 of the fluidic tee 46 under the control of a needle drive 60. In addition to controlling the movement and position of the injection needle 58 into and out of the seat 70 of the fluidic tee 46, the needle drive 60 can also move the injection needle 58 in an angular direction.

The online sampling valve 34 has six fluidic ports 34-1, 34-2, 34-3, 34-4, 34-5, and 34-6 and three flow-through conduits 34-11, 34-12, and 34-13. Fluidic ports 34-1 and 34-2 are plugged and not used for sample flow, essentially dead-ending the connected tubes. Tubing connects fluidic port 34-3 to fluidic port 32-1 of the priming valve 32. Tubing connects fluidic port 34-4 to the injection needle 58. Further, tubing connects fluidic port 34-5 to the external sampling assembly 6. In the system idle configuration and as shown in FIG. 3, the flow-through conduit 34-13 provides a fluidic pathway between fluidic ports 34-5 and 34-6, thereby providing a continuous fluidic pathway between the external sampling assembly 6 and the first waste reservoir 54.

Similarly, as shown in the figures, the process valve 36 has six fluidic ports 36-1, 36-2, 36-3, 36-4, 36-5 and 36-6 and two flow-through conduits 36-11 and 36-12. Fluidic ports 36-5 and 36-6 are plugged. Tubing connects fluidic port 36-1 to the process valve 36 to the process pump 44. Further, tubing connects fluidic port 36-2 to a first wash reservoir 50. Also, tubing connects the external sampling assembly 6 to fluidic port 36-3 of the process valve 36. Tubing connects fluidic port 36-4 to the process pump 44.

Further shown in the figures, the injection valve 38 has six fluidic ports 38-1, 38-2, 38-3, 38-4, 38-5 and 38-6, three flow-through conduits 38-11, 38-12 and 38-13, and a second sample loop 64. The second sample loop 64 is connected to the fluidic ports 38-4 and 38-1. Tubing connects fluidic port 38-2 to a third waste reservoir 56. Tubing connects fluidic port 38-3 to the fluidic tee 46. Further, tubing connects the solvent delivery system 12 to fluidic port 38-5. Also, tubing connects fluidic port 38-6 to the column 86. When the system is idle, flow-through conduit 38-11 provides a fluidic pathway between fluidic ports 38-1 and 38-6. Likewise, flow-through conduit 38-12 provides a fluidic pathway between fluidic ports 38-2 and 38-3 and flow-through conduit 38-13 provides a fluidic pathway between fluidic ports 38-4 and 38-5. The solvent delivery system 12 is on in order to maintain minimal disturbance to the solvent composition stream. Hence, the solvent composition stream continuously flows. In the idle position, the solvent composition stream flows into fluidic port 38-5 through flow-through conduit 38-13 out fluidic port 38-4 through the second sample loop 64 into fluidic port 38-1 through flow-through conduit 38-11 and out fluidic port 38-6 to the column 86. The PSM 4 allows injections of 1, 2, and 5 µl. The injection valve 38 can provide larger injections, but that would require drawing a larger volume from the process. The transducers are active and allow the PSM 4 to monitor the pressure during the dilution and/or quenching of the sample to ensure that the sampling, dilution, quenching and injection were performed properly. The first, second and third transducers 102, 104 and 106 each allow the sampling system 2 to monitor pressure during the draw and discharge cycling. High pressure during draw indicates blockage on the inlet side. On the other hand, low pressure on the delivery side indicates a leak. High pressure on the delivery side also indicates a blockage on the outlet side. The signals are acquired and monitored by the PSM 4. The pressure limits are preferably set in the Empower instrument and transferred to the PSM 4 at the beginning of a run.

More specifically, transducers 102, 104, 106 can monitor the process pump 44 and also diluent and sample flow into and out of the online sampling valve 34. The transducers 102, 104, 106 of the process sample manager 4 use a strain gauge to translate the pressure into an electrical signal. Pressure or vacuum (sometimes referred to as negative pressure) can then be read. The signal provided by the pressure transducers in the process sample manager 4 provides for monitoring, sampling and drawing of diluent for blockages (i.e. high vacuum) and the dilution/quenching and injection for blockages (high pressure). Either of these faults would cause the process sample manager 4 to stop since they would compromise the performance of the process sample manager 4. A high pressure could mean that the liquid being pushed is not delivered where it is meant to go or that the flow rate is too high. A high vacuum could indicate that the sample is too viscous for the flow rates used during the draw of the sample or diluent.

This sampling system 2 in combination with the liquid chromatography 2 or mass spectrometry system (not shown) can be used to monitor any process or reaction where the reactor or the reactor flow stream is near or far away from the process sample manager 4.

The maximum distance between the reactor 22 or reactor flow stream (not stream) and the process sample and dilution system 20, i.e., the length of tubing between those two systems, can be mathematical represented as follows: $\Delta p = 8 * \rho * (V^2) / (\pi^2 * D^4) * \lambda * L / D * 0.00014504$, where $\rho$ = solvent density (kg/m$^3$)
$V$ = flow velocity (m$^3$/s)
$D$ = tube diameter (m)
$\lambda$ = Coefficient of friction
$L$ = length of tube
0.00014504 = Pa to psi.

Sample volume must be large enough to be transferred from the reactor 22 to the injection valve 38. In the present system 20, sample flow is largely undisturbed and unaffected by the system 20. If sample is first diluted, a larger volume is created and sample can be transferred farther. Because tubing diameters are narrow, sample diffusion is minimized regardless of distance transferred. In the present systems, samples largely remain intact because contact area between sample and solvent is minimized. Diffusion of any sample at the edges of the tubing, however, can go to waste and is not part of a representative sample. With the use of a backwash in the system 20, dispersion of the sample is avoided. In addition, the amount of sample required for the column 86 or the detector (not shown) is minimized because of the low rate of dispersion of sample into the wash.

Sample is drawn from a source of sample that is not operating under pressure, i.e., not operating under pressures greater than about 1 atmosphere or 14.7 psi at sea level, and is sometimes referred to herein as a "non-pressurized" source of sample such as a non-pressurized reactor 22, non-pressurized reactor stream, or a non-pressurized reaction. The process sample manager 4 can dilute a sample at the fluidic tee 46.

Sampling System: Sample Flow

Figure 4:
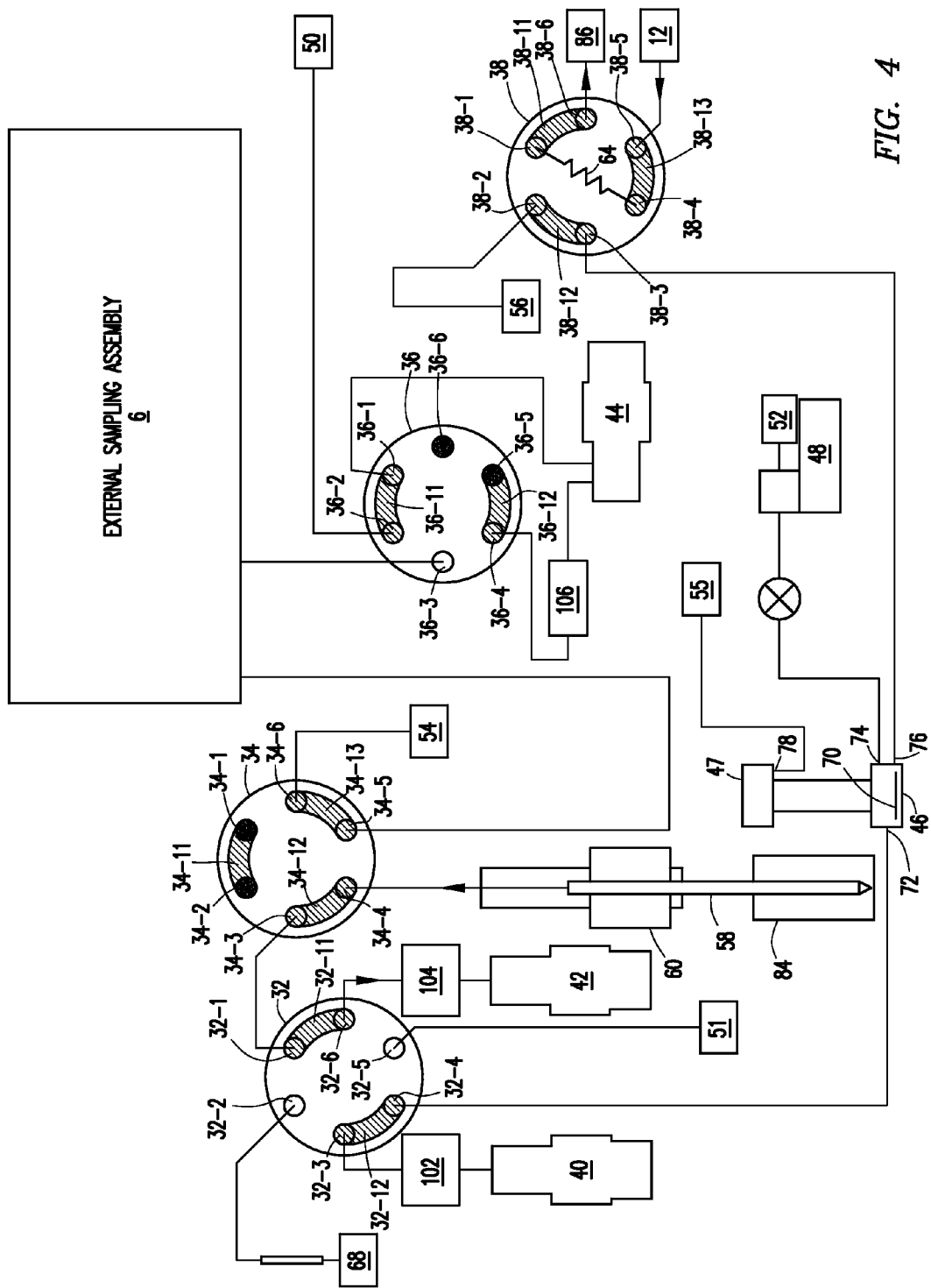
FIG. 4 shows the sampling system configured to calibrate system with calibration solution drawn from vial.
Figure 5:
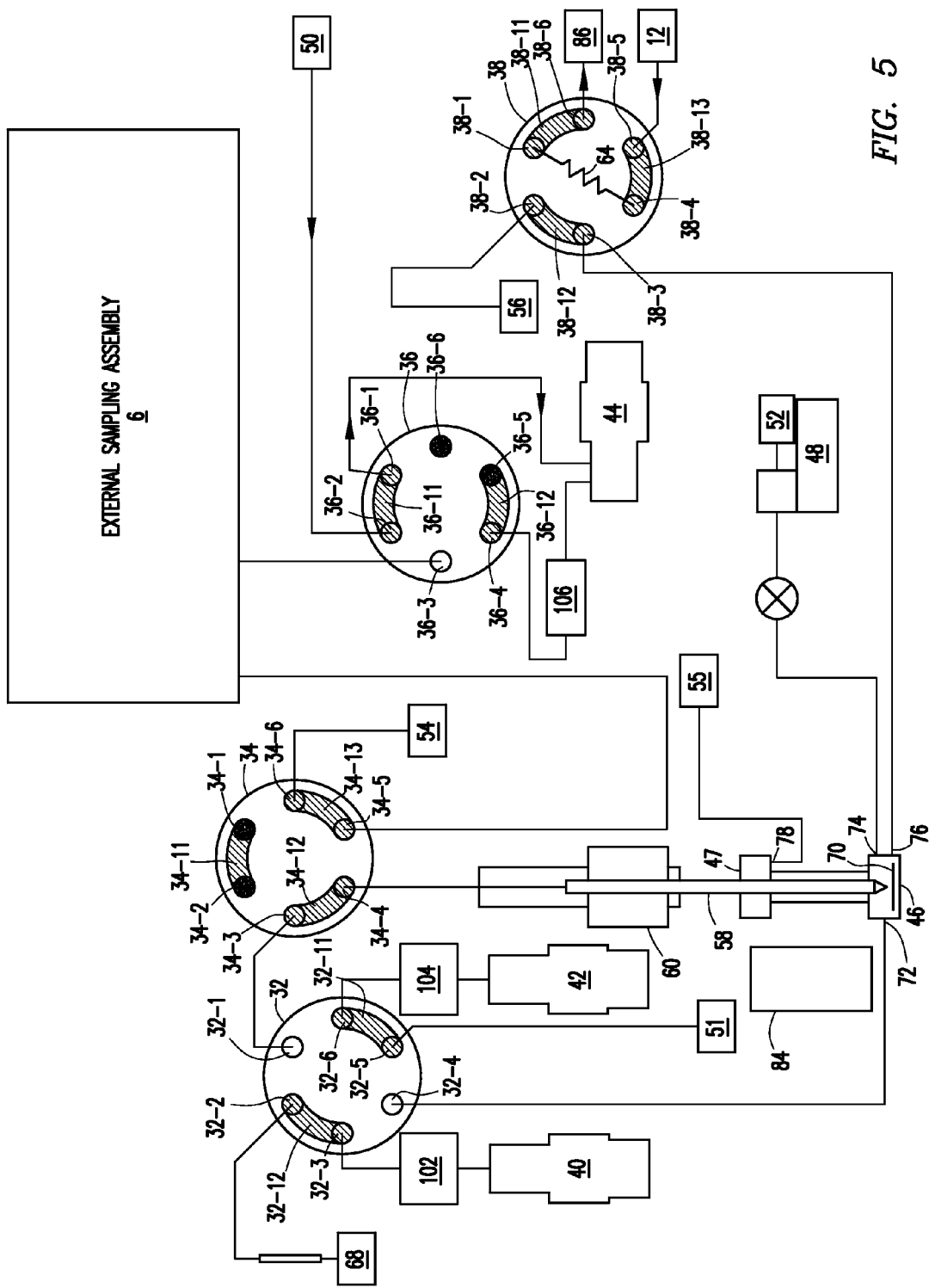
FIG. 5 shows the sampling system configured to draw wash from the first wash reservoir into the process valve.
Figure 6:
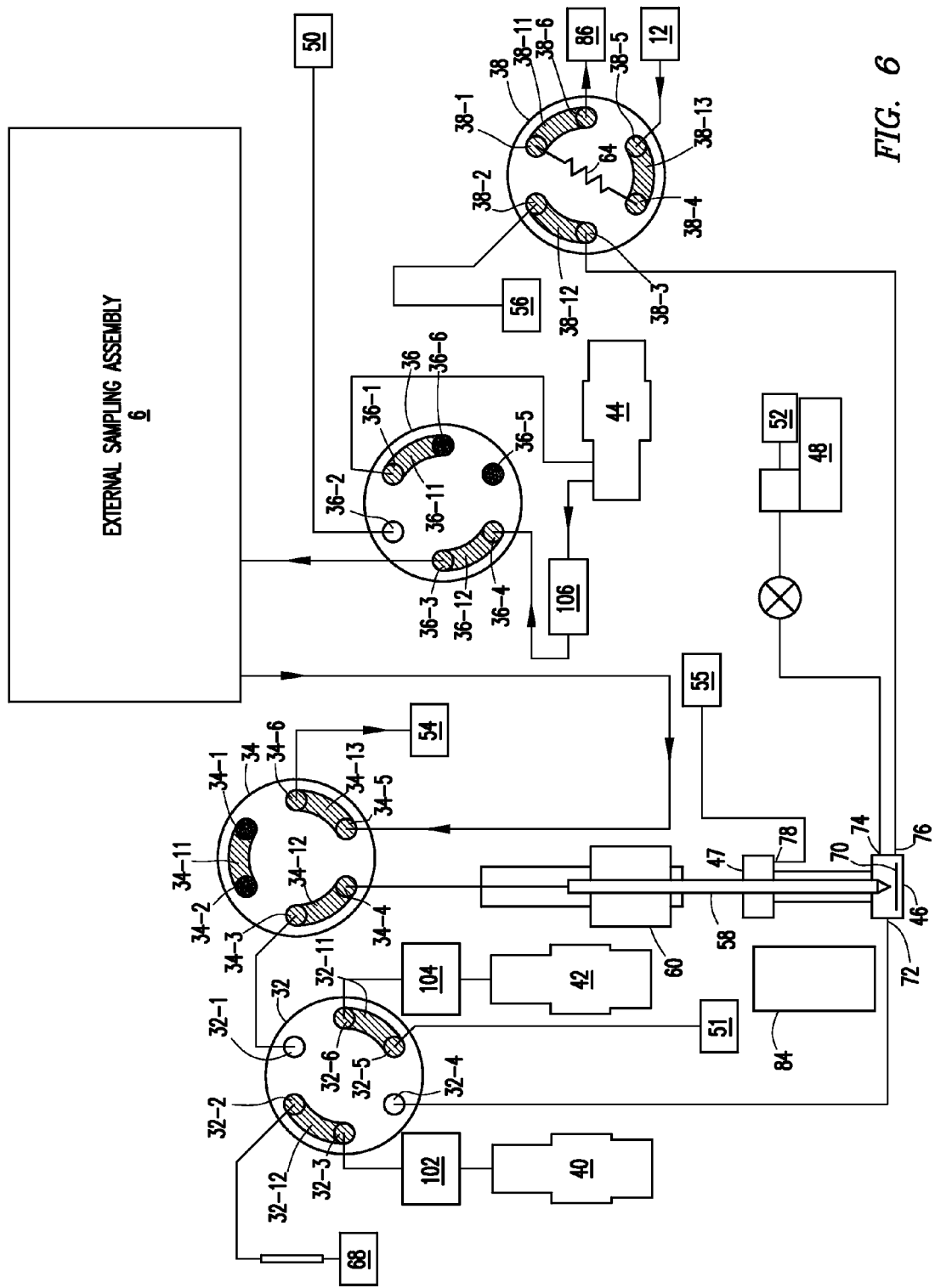
FIG. 6 shows the sampling system configured to move sample to the online sampling valve.
Figure 7:
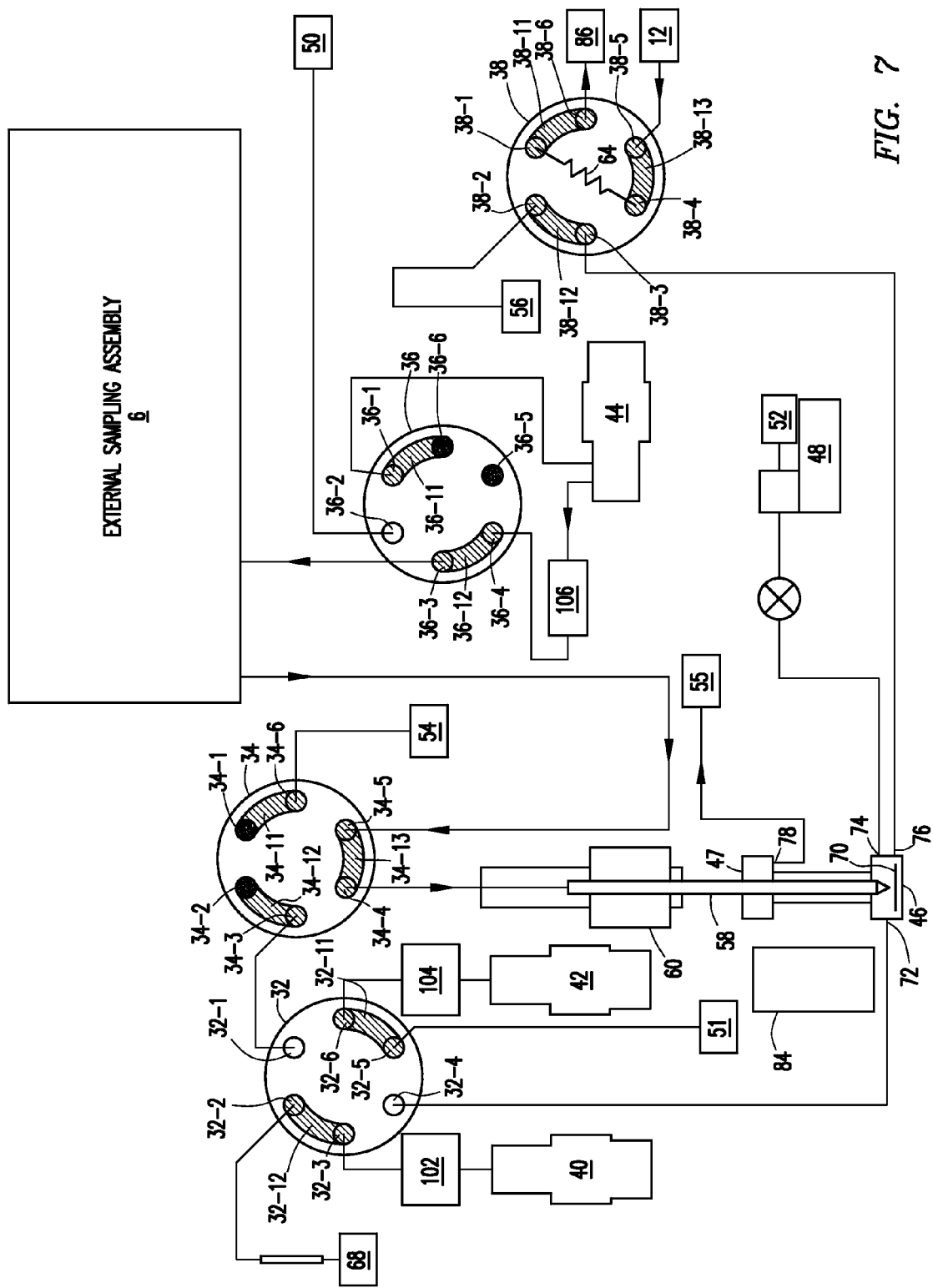
FIG. 7 shows the sampling system to fill the needle with sample.
Figure 8:
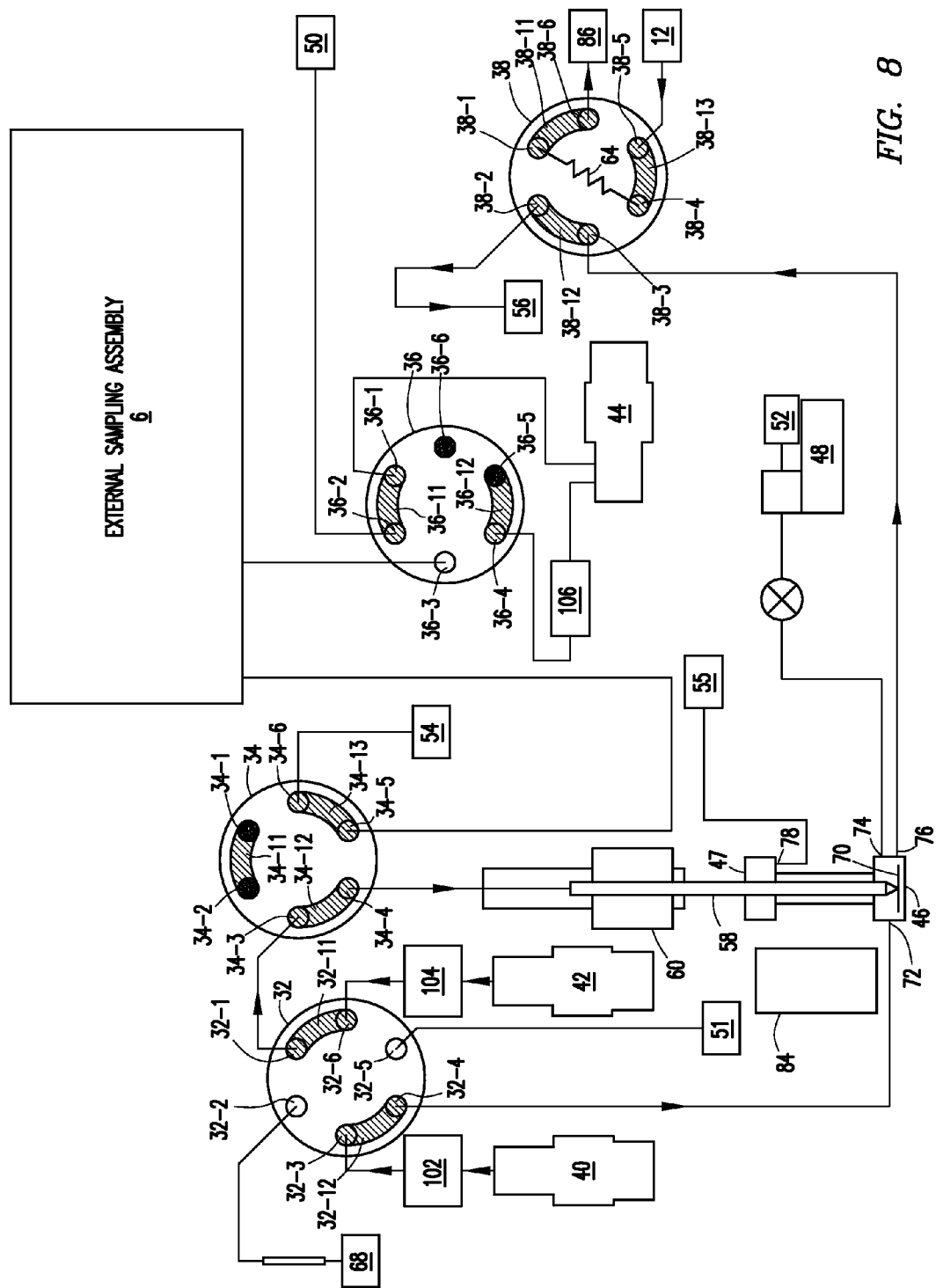
FIG. 8 shows the sampling system configured to dilute sample.
Figure 9:
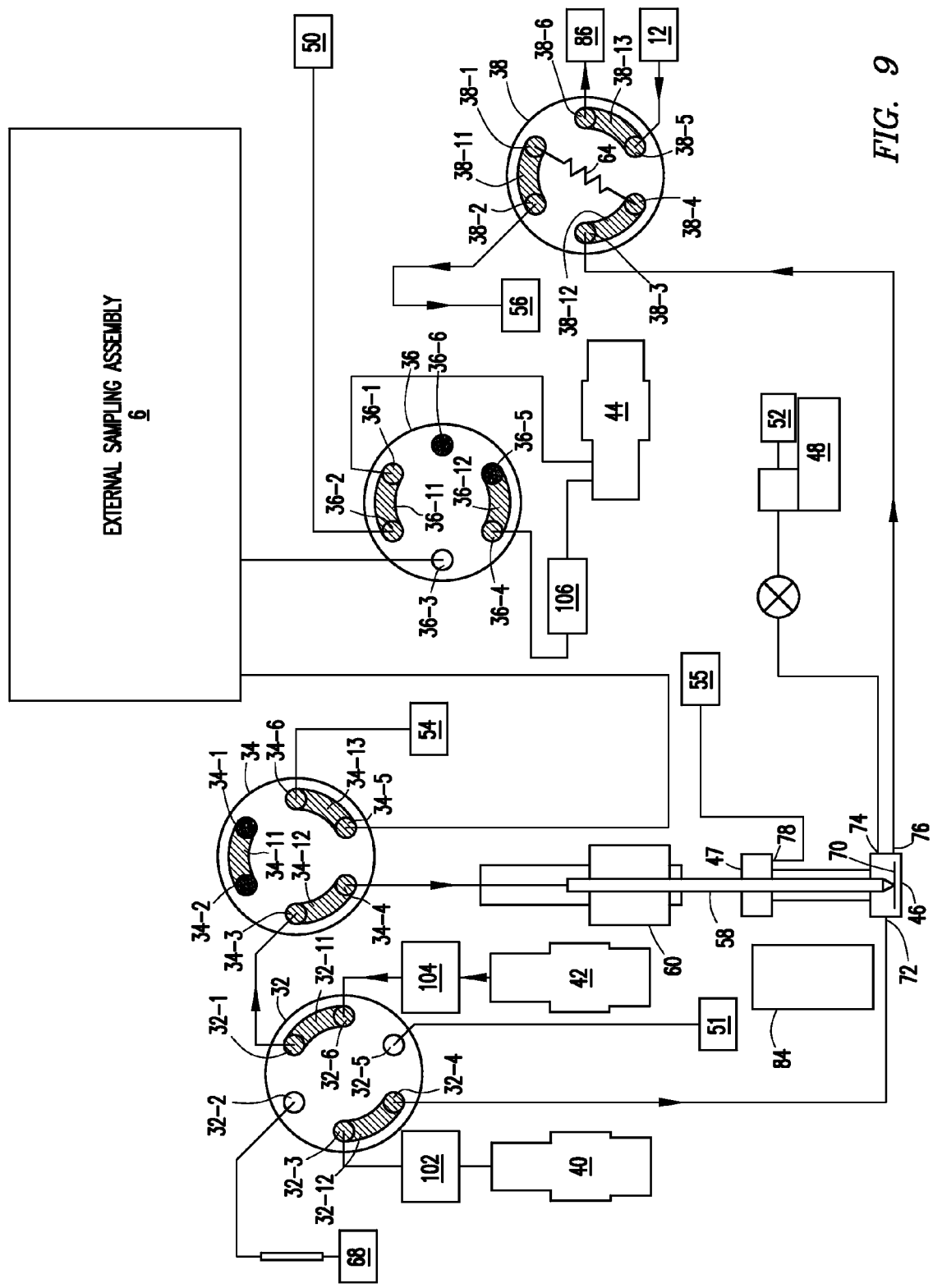
FIG. 9 shows the sampling system configured to load sample into the second sample loop of the injection valve.
Figure 10:
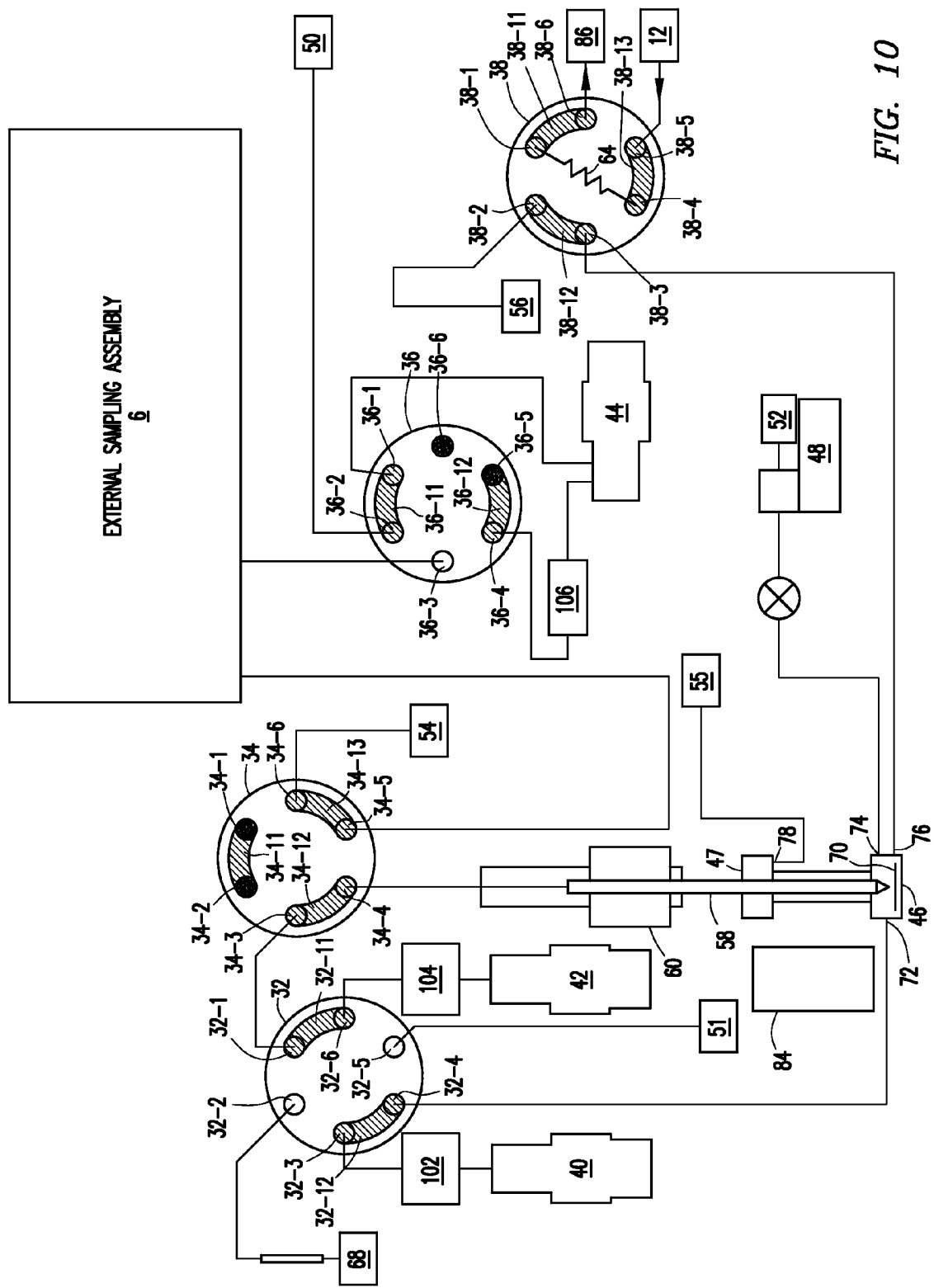
FIG. 10 shows the sampling system configured to inject sample into the solvent composition stream.
Figure 11:
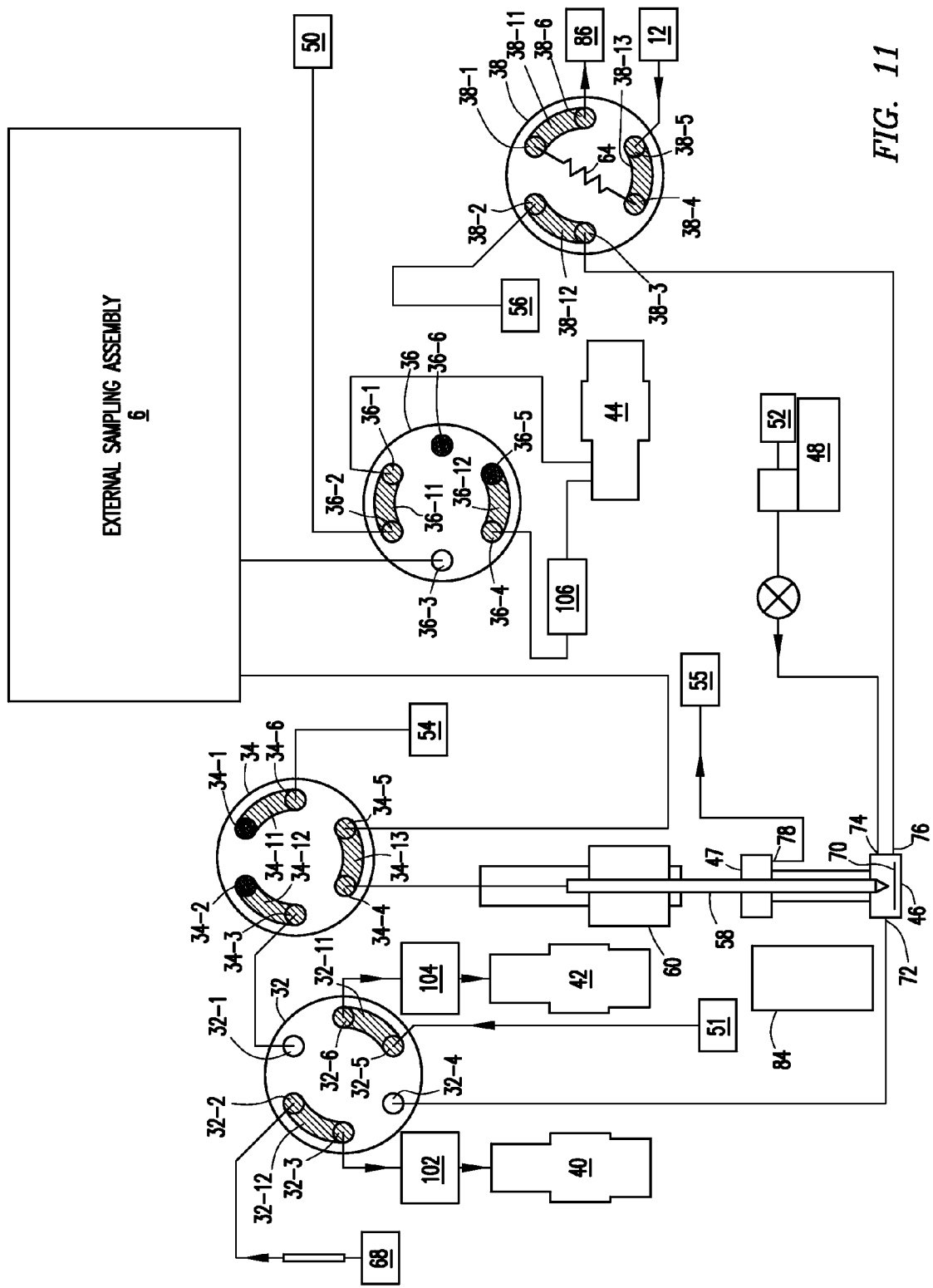
FIG. 11 shows the sampling system configured to wash fill.
Figure 12:
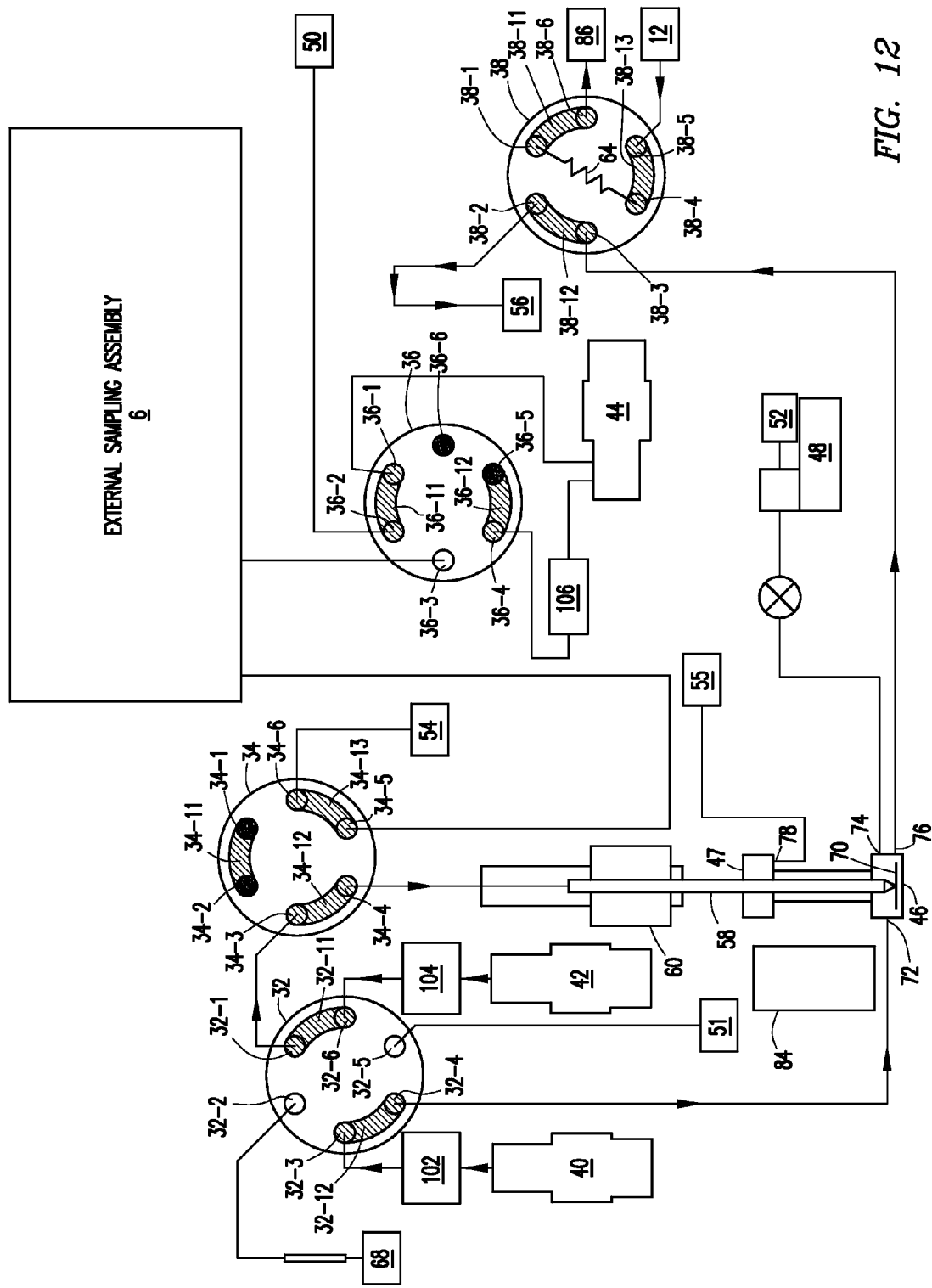
FIG. 12 shows the sampling system configured to empty the wash fill.
Figure 13:
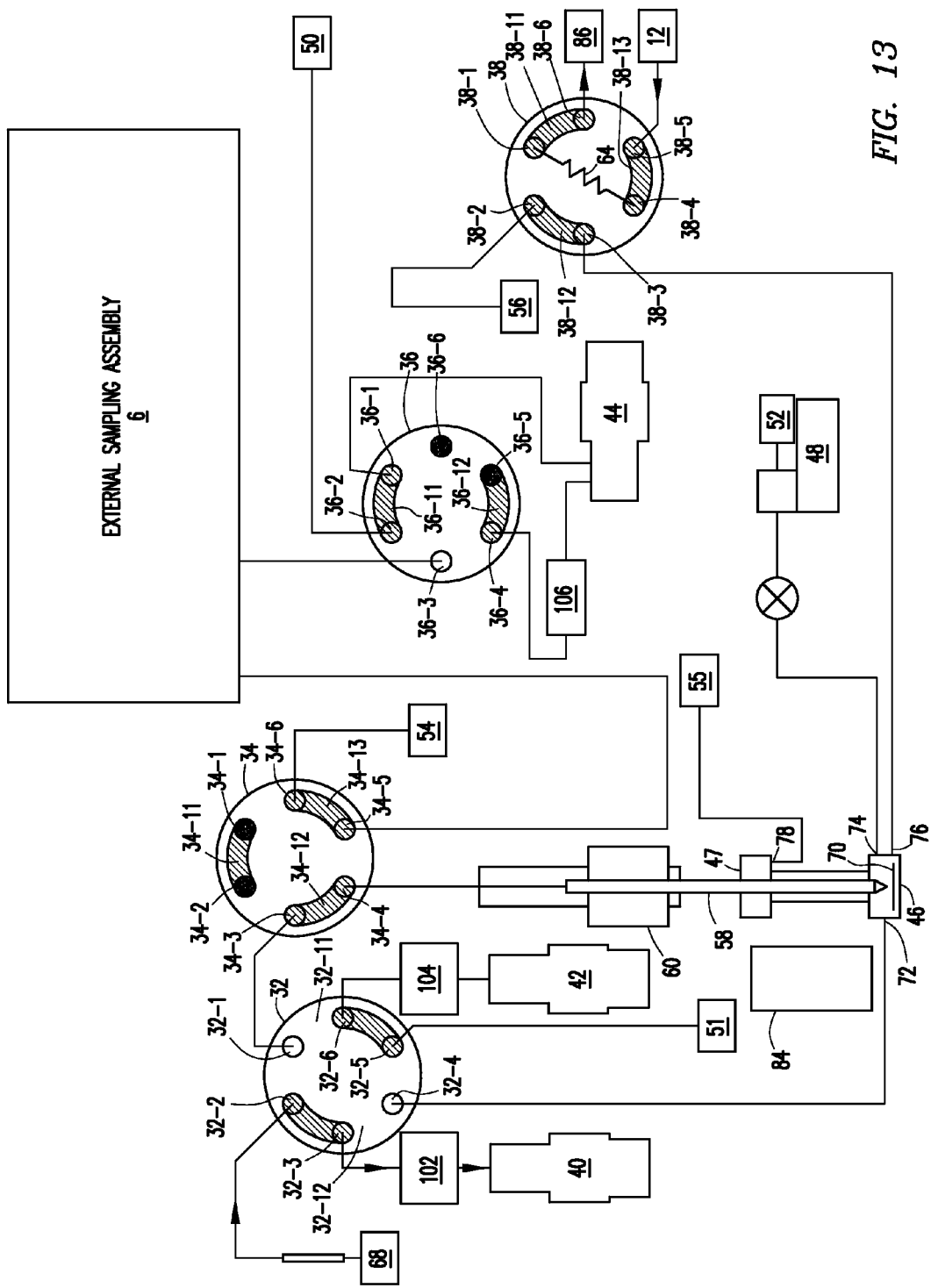
FIG. 13 shows the sampling system ready for the next injection.

As shown in the figures and described in more detail below, the sampling system 2 can be calibrated by drawing a calibration solution ("a calibration standard") from a vial 84 (FIG. 4). When the external sampling valve 24 is in the first configuration, the external pump 28 is turned on, drawing sample from the reactor 22 into the external sampling valve 24 (FIG. 2A). The process pump 44 is then charged drawing wash from the first wash reservoir 50 into the process valve 36 (FIG. 5). In the second configuration, the external sampling valve 24 can discharge sample into the first sample loop 62 and recirculate sample back to the reactor 22 (FIG. 2B). The configuration of the external sampling valve 24 returns to the first configuration (FIG. 2A) and the process pump 44 discharges wash from the process valve 36 backwashing and moving sample to the online sampling valve 34 of the process sample manager 4 (FIG. 6). Optionally, a small portion of the sample may flow into the first waste reservoir 54. Sample is then loaded into the injection needle 58 of the process sample manager 4 (FIG. 7). Sample is diluted at the fluidic tee 46 of the process sample manager 4 where the process pump 44 is turned off and the diluent pump 40 and the sample pump 42 are on (FIG. 8). Sample is then sent to the injection valve 38, loaded and injected into the solvent composition stream pumped from the solvent delivery system 12 (FIG. 9). The sample in the solvent composition stream flows to the column 86 (FIG. 10). Subsequently, the sampling system 2 undergoes a wash fill and the diluent pump 40 and sample pump 42 are recharged (FIG. 11). Wash is emptied from the process sample manager 4 (FIG. 12). The diluent pump 40 is refilled and ready for the next injection (FIG. 13).

There are many advantages of the methods and systems disclosed herein. First, while volume of sample must be large enough to move sample from the reactor 22 to the process sample manager 4, sample flow is largely undisturbed and not effected by the system 2. If the sample can be diluted, a larger sample volume is created and can be moved farther. However, the tubing throughout the system 2 is very small and therefore minimizes sample diffusion. Sample travels in the middle of the tubular flow and, therefore, diffusion of sample at the edges of the tubing goes to waste and is not representative of sample. The volume of sample that is diffused is minimized and dispersion of the sample avoided. The sample largely remains intact. In addition, the amount of sample required for the detector is minimized because of the low rate of dispersion of sample into the wash.

System Calibration

FIG. 4 depicts the external sampling assembly 6 configured for calibration. As described above, to calibrate the system, calibration solution (a standard) is drawn from the vial 84. Here, the sample pump 42 is turned on to draw solution through the online sampling valve 34 and the priming valve 32. The priming valve 32 is configured so that the flow-through conduit 32-11 provides a fluidic pathway between fluidic ports 32-1 and 32-6 and flow-through conduit 32-12 provides a fluidic pathway between fluidic ports 32-3 and 32-4. The sample pump 42 is turned on so to draw from the vial 84 as shown by the arrows between the sample pump 42 and the priming valve 32, and the online sampling valve 34 and the needle drive 60. The diluent pump 40 is off. The external pump 28 and the process pump 44 can be on or off.

Standards or at-line samples are drawn into the injection needle 58. This calibration run allows the user to know the system responds to a known standard or calibrant (same as the process sample or similar). The standard can be injected or diluted depending on the user's need. The fluidics of the PSM 4 treat the dilution of a standard/at-line sample the same way as an on-line injection. For these reasons, the calibration run can predict exactly the response of an at-line or on-line sample. A standard (also referred to as calibrant) is typically the same as the process sample or similar in chemical constitution and response. The injection needle 58 moves out of the vial 84 and into the fluidic tee 46.

Sampling From a Single Reactor

For sampling from a single reactor 22, after the calibration step, the external pump 28 and the process pump 44 are turned on. As described above, the external sampling valve 24 toggles between two configurations, the first configuration and the second configuration as described herein and in three steps: draw sample, load sample and discharge sample. First, in the first configuration as shown in FIG. 2A, sample is drawn by the external pump 28 from the reactor 22. In the second configuration shown in FIG. 2B, sample is loaded into and fills the first sample loop 62 and is recirculated back to the reactor 22. Third, by rotating counterclockwise one port position, the external sampling valve 24 is returned to the first configuration of FIG. 2A and sample is flushed from the first sample loop 62 to the process sample manager 4.

More specifically, as described above, FIGS. 2A and 2B shows the first and the second configurations of external sampling valve 24 used to draw sample from a single reactor 22. Specifically, as shown in FIG. 2A, in the first configuration, sample is drawn from the reactor 22 flowing through fluidic port 24-10, fluidic conduit 24-15 and out fluidic port 24-9 to the external pump 28. As shown in FIG. 2B, in the second configuration, the external sampling valve 24 has been rotated one port position clockwise. In the second configuration, sample flows from the external pump 28 into fluidic port 24-7 through fluidic conduit 24-14 and out fluidic port 24-6. Sample fills the first sample loop 62 into fluidic port 24-3 through fluidic conduit 24-12 and out fluidic port 24-2 recirculating back to the reactor 22. Sample constantly flows through the first sample loop 62 in this manner. The external sampling valve 24 then rotates counterclockwise toggling back to the first configuration. The external pump 28 displaces sample drawn through the first sample loop 62 and back to the reactor 22. The process pump 44 pumps wash to the external sampling valve 24 to flush sample out of the first sample loop 62 to the process sample manager 4. If the process pump 44 is not turned on, sample will recirculate only. To send sample to the process sample manager 4, the external pump 28 and process pump 44 are turned on and charged.

Drawing Sample from Multiple Reactors

Samples can be taken from one or more sources (reactors, reactor flow streams, and the like) sequentially or simultaneously, in series or in parallel. Each external sampling valve 24 draws sample independently from the other. However, the number of samples that can be taken depends on the number of external sampling valves 24 provided in the external sampling assembly 6. Also, for each external sampling valve 24, an external pump 28 is provided. Further, if a plurality of external sampling valves 24 is required, there must be two selection valves 26 and there can be up to six external sampling valves 24 for every two selection valves 26.

To draw sample from multiple reactors 22 or other sources, the external pump 28 must be on. As described above and shown in FIGS. 2A and 2B, the external sampling valves 24 alternate between two configurations and do so, in three steps. Each of the external sampling valves 24 can be in the same configuration or can be in the other configuration, i.e., the first configuration versus the second configuration described above.

By way of example, FIG. 3 shows the external sampling assembly 6 having three external sampling valves 24 and two selection valves 26. As shown in FIG. 3, the external sampling valves 24 can be in different configurations. In this example, sample can be drawn from the reactor 22 through fluidic port 24-10, flow-through conduit 24-15 and out fluidic port 24-9 of the external sampling valve 24. Concurrently, sample could be displaced in the first sample loop 62 of another external sampling valve 24 and recirculated to reactor 22. In addition, at the same time, another external sampling valve 24 could return to its first configuration where sample flows out of port 24-12 of the external sampling valve 24 through the selection valve 26 to the process system manager 4.

In general, the selection valves 26 has six fluidic ports 26-1, 26-2, 26-3, 26-4, 26-5 and 26-6 that may be connected to a plurality of external sampling valves 24 as the user sees fit. Fluidic port 26-7 of the selection valve 26 is connected to the online sampling valve 34 of the process sample manager 4. As shown in FIG. 3, wash can be discharged by the process pump 44 through the selection valve 26 to the external sampling valve 24 through fluidic port 26-7. The sample is then backwashed to flow into the selection valve 26 at one of the six fluidic ports 26-1, 26-2, 26-3, 26-4, 26-5 and 26-6 out to the process sample manager 4 at fluidic port 26-7.

Drawing Wash and Diluent into the Process Sample Manager

FIG. 5 shows the sampling system 2 configured to draw wash from the first wash reservoir 50 into the process valve 36. The process pump 44 and the external pump 28 are turned on and charged, and the configuration of the priming valve 32 is changed. The priming valve 32 is rotated clockwise one port position from that shown in FIG. 4 (calibration step) allowing the diluent pump 40 to draw diluent from the diluent source 68. Diluent flows into the priming valve 32 at fluidic port 32-2 into flow through conduit 32-12 and out fluidic port 32-3. Similarly, wash is drawn from the first wash reservoir 50 into the process valve 36 at fluidic port 36-2, and a fluidic pathway is provided through the flow-through conduit 36-11 and out fluidic port 36-1 to the process pump 44. As noted above, sample is constantly flowing through the first sample loop 62. While sample may not be returned directly to the reactor 22 for most processes, recycle systems and devices can be connected directly to the external sampling valve 24 to allow for the sample to flow back to the reactor 22, with or without further treatment or processing of the sample.

Sample to the Online Sampling Valve of the Process Sample Manager

FIG. 6 depicts the sampling system 2 configured to move sample to the online sampling valve 34. As shown in FIG. 6, the process valve 36 is rotated one position clockwise. The process valve 36 is then configured so that the flow-through conduit 36-12 provides a fluidic pathway between the fluidic ports 36-3 and 36-4. Process pump 44 discharges wash from the process valve 36 to the external sampling valve 24 pushing sample through the first sample loop 62 and out to the online sampling valve 34 of the process sample manager 4. When selection valves 26 are part of the external sampling assembly 6 as in the case of sampling from multiple sources, the process pump 44 discharges wash from the process valve 36 to the external sampling valve 24 and via the selection valve 26 to the online sampling valve 34 of the process sample manager 4. Any diffused sample and/or any excess sample drawn flows to the first waste reservoir 54. The priming valve 32, the online sampling valve 34, and the injection valve 38 remain in the same configuration as shown in FIG. 5.

Sample to the Injection Needle of the Process Sample Manager

FIG. 7 shows the sampling system 2 having the valves configured to move the drawn sample into the injection needle 58. To fill the needle 58 with sample, the configurations of the priming valve 32, the process valve 36, the injection valve 38, and the external sampling valve 24 (not shown) do not change and remain as shown in FIG. 6. Similarly, the external pump 28 and process pump 44 remain on to continue to push sample out of the external sampling valve 24 and to dilute the sample in the fluidic tee 46, respectively.

As shown in FIG. 7, the online sampling valve 34 is turned clockwise by one port position (alternatively, a counterclockwise rotation achieves an equivalent configuration) such that the flow-through conduit 34-12 or flow-through conduit 34-13 connects the fluidic port 34-4 to the fluidic port 34-5, and thereby connects the external sampling assembly 6 to the injection needle 58 as shown by the arrows. Because both fluidic ports 34-1 and 34-2 are plugged, there are no pathways for fluidic flow through the online sampling valve 34 via fluidic port 34-11 or fluidic port 34-12. The injection needle 58 lifts off the seat 70 if sample bubbles up within the fluidic tee 46. As described below and shown in FIG. 11, a wash pump 48 then draws wash from a third wash reservoir 52 connected to the fluidic tee 46 to wash the injection needle 58. The wash flows into a second waste reservoir 55 also connected to the fluidic tee 46.

Sample Dilution

FIG. 8 shows the sampling system 2 configured to dilute sample in the process sample manager 4. The configuration of the injection valve 38 is unchanged from the drawing sample configuration shown in FIG. 7. As an option, the configuration of the process valve 36 changes to the configuration that is shown in FIG. 8 or remains in the optimal configuration as shown in FIG. 7. Notwithstanding, the configurations of the priming valve 32 and the online sampling valve 34 are changed. Also, as an option, the configuration of the external sampling valve 24 (not shown) remains. However, optimally, configuration of the external sampling valve 24 can change as well as the configuration of the selection valve 26. The ability to move the external sampling valve 24 and the selection valve 26 allow the sampling system 2 to sample from the reactor 22 or reactor stream while diluting and injecting the sample previously drawn.

As shown in FIG. 8, the process valve 36 is turned counter-clockwise by one port position such that flow-through port conduit 36-12 connects fluidic port 36-4 to 36-5 and flow-through conduit 36-11 connects fluidic port 36-1 to 36-2. Fluidic port 36-5 and fluidic port 36-6 are plugged. On the other hand, the priming valve 32 is rotated counterclockwise one port to provide diluent flow from the diluent source 68. Flow-through conduit 32-12 connects fluidic ports 32-3 and 32-4 to provide a fluidic diluent pathway to the fluidic tee 46. This is depicted on FIG. 7 via arrows pointing out of the diluent pump 40 into the priming valve 32 and out to the fluidic tee 46. Similarly, flow-through conduit 32-11 connects fluidic port 32-1 and fluidic port 32-6 to provide a fluidic pathway from the sample pump 42 to the online sampling valve 34. The sample pump 42 pushes wash out of the priming valve 32 through fluidic port 32-6 to fluidic port 32-1 via flow-through conduit 32-11 as shown by the arrows.

Further, as shown in FIG. 8, the online sampling valve 34 is rotated by one port position either counterclockwise as shown in FIG. 7 or clockwise (not shown). Flow-through conduit 34-12 connects the fluidic port 34-3 to the fluidic port 34-4 and together with the flow-through conduit 32-11 of the priming valve 32 provides a continuous fluidic pathway between the sample pump 42 and the injection needle 58. The needle drive 60 positions the injection needle 58 in the seat 70 of fluidic tee 46 and the sample pump 42 pushes the previously drawn wash through flow-through conduit 34-12 into the injection needle 58 as illustrated by arrows.

Essentially, wash displaces sample causing the sample within the injection needle 58 to enter the fluidic tee 46, as illustrated by arrows. The fluidic tee 46 operates to merge and mix sample through the injection needle 58 with diluent entering the fluidic tee 46 at the first inlet 72. The diluted sample leaves the fluidic tee 46 through the first outlet 76 and travels to the fluidic port 38-3 of the injection valve 38, as illustrated by arrows between the same. Any overfill of sample passes to a third waste reservoir 56 from the fluidic port 38-3 through the flow-through conduit 38-12 and out through the fluidic port 38-2.

To dilute the sample, the diluent pump 40 and the sample pump 42 move fluids concurrently. The flow rates of these pumps determine the dilution ratio (overall dilution flow rate to process sample flow rate). Consider, for example, an overall dilution flow rate of 100 µl/min, with the sample pump 42 pushing 10 µl/min while the diluent pump pushes 90 µl/min: the result is a 10:1 dilution. For example, when the sample pump 42 pushes 50 µl/min, while the diluent pump 40 pushes 50 µl/min, the result is a 2:1 dilution.

Sample Loaded into Injection Valve

FIG. 9 shows the sampling system 2 having valves configured to load sample into the second sample loop 64 of the injection valve 38. The configurations of the priming valve 32 and the online sampling valve 34 are the same as those from those shown in FIG. 8. Similarly, the configurations of the process valve 36 and the external sampling valve 24 remain in the optimal configurations of FIG. 8. However, the configuration of the injection valve 38 is changed. The injection valve 38 is rotated counter-clockwise by one port position. Continued operation of the sample pump 42 pushes the sample into the second sample loop 64, as illustrated by arrows between the fluidic tee 46 and the injection valve 38. The diluent pump 40 and process pump 44 are off.

More specifically, the flow-through conduit 38-12 connects fluidic port 38-3 to fluidic port 38-4 to provide a continuous fluidic pathway from the first outlet 76 of the fluidic tee 46 through the second sample loop 64 into fluidic port 38-1 of the flow-through conduit 38-11 out of fluidic port 38-2 to the third waste reservoir 56 and capturing any overfill of the second sample loop 64. In addition, flow-through conduct 38-13 connects fluidic port 38-5 to fluidic port 38-6 for a continuous flow of solvent composition stream from the solvent delivery system 12 to the column 86.

Sample Injected into Column

FIG. 10 shows the sampling system 2 having valves configured to inject the sample into the column 86. Here, sample is mixed with the solvent composition stream arriving at the injection valve 38 from the solvent delivery system 12. The configuration of the priming valve 32, the online sampling valve 34, the process valve 36, the external sampling valve 24, and the external process valve 26 are unchanged from those of configured to load the sample into the second sample loop 64 within the injection valve 38 shown in FIG. 9. The configuration of the injection valve 38, however, changes.

To introduce the diluted sample to the solvent composition stream, the injection valve 38 is rotated clockwise by one port position from its position shown in FIG. 8 (i.e., back to the position of FIG. 8) such that the flow-through conduit 38-11 connects the fluidic port 38-1 to the fluidic port 38-6 and the flow-through conduit 38-13 connects the fluidic port 38-5 to fluidic port 38-4. This configuration places the second sample loop 64, and the sample contained therein, in the path of the solvent composition stream arriving from the solvent delivery system 12. In this manner, the diluted process sample is introduced to the solvent composition stream.

System Wash Fill

FIG. 11 shows the sampling system 2 having the valves configured to wash fill. The configurations of the process valve 36, the injection valve 38 and the external sampling valve 24 are unchanged from the configuration shown in FIG. 10. However, the configuration of the priming valve 32 and the online sampling valve 34 are changed.

The priming valve 32 is rotated one port position such that flow-through conduit 32-11 connects fluidic port 32-5 to fluidic port 32-6, thereby fluidically connecting the second wash source 51 to the sample pump 42. Also, fluidic conduit 32-12 connects fluidic port 32-2 to fluidic port 32-3, thereby connecting the diluent source 68 with the diluent pump 40. The online sampling valve 34 is rotated one port position such that flow-through conduit 34-13 connects fluidic port 34-4 to fluidic port 34-5. Flow-through conduct 34-12 connects fluidic port 34-6 to plugged fluidic port 34-1, and flow-through conduit 34-11 connects plugged fluidic port 34-2 to fluidic port 34-3. During this phase, the injection needle 58 is lowered into the wash tower 47 and the fluidic tee 46. The diluent pump 40 and the sample pump 42 are recharging and being filled. The diluent pump 40 draws diluent into the priming valve 32 as shown by the arrow between the diluent source 68 and the priming valve 32, and the arrow between the priming valve 32 and the diluent pump 40. The sample pump 42 is turned on to draw in wash from the second wash reservoir 51. The wash pump 48 is also turned on to draw wash from the third wash reservoir 52 and wash the wash tower 47, the injection needle 58 and the fluidic tee 46, pushing the wash through to the second waste reservoir 55. Subsequently, after the sample pump 42 washes its fluidic circuit with sample or wash.

System Wash Clean and Empty

FIG. 12 shows the sampling system 2 having the valves configured to empty wash from the pumps and generally clean out the tubing. The configurations of the process valve 36, the injection valve 38 and the external sampling valve 24 are unchanged from the configuration to run a wash fill as set out in FIG. 11. However, the configurations of the online sampling valve 34 and the priming valve 32 are changed. Here, the online sampling valve 34 is rotated one port position such that fluidic conduit 34-11 connects plugged fluidic port 34-1 to plugged fluidic port 34-2. Flow-through conduit 34-12 connects fluidic port 34-3 to fluidic port 34-4, and flow-through conduit 34-13 connects 34-5 to 34-6 providing a continuous fluidic pathway from the priming valve 32 through the injection needle 58 to the seat 70 of the fluidic tee 46 as shown by the arrows.

Likewise, the priming valve 32 is rotated one port position such that flow-through conduit 32-11 connects fluidic port 32-1 to fluidic port 32-6 and flow-through conduit 32-12 connects plugged fluidic port 32-3 to fluidic port 32-4 providing a continuous fluidic pathway from sample pump 42 through the priming valve 32 to the online sampling valve 34 as shown by the arrows. During this phase, the diluent pump 40 and the sample pump 42 are both pumping. As a result, both the diluent pump 40 and the sample pump 42 are connected to the fluidic tee 46 and the injection valve 38 where sample can flow through to the third waste reservoir 56. Noteworthy is the fact that it takes 3 to 5 times the pump volume to wash a pump out. However with the systems and methods disclosed herein, sample is not sent to the pumps. Therefore, pump 28, pump 40 or pump 44 does not contain sample and less sample is used. So, it is not necessary (although always an option) to wash out the pump.

Pump Refill

FIG. 13 shows the sampling system 2 having valves configured to refill diluent pump 40 and get ready for the next injection. The configurations of the online sampling valve 34, the process valve 36, the injection valve 38, and the external sampling valve 24 are unchanged from the empty wash configuration of FIG. 12. However, the priming valve 32 is changed by rotating the valve one port position. Optionally the configuration of the external process valve 26 is changed. As further shown in FIG. 12, the priming valve 32 is also configured so that diluent pump 40 is ready to draw diluent from the diluent source 68. Here, flow-through conduit 32-12 connects fluidic port 32-2 to fluidic port 32-3 and flow-through conduit 32-11 connects fluidic port 32-6 to fluidic port 32-5.

The External Sampling Assembly: A Trace Enrichment Device

The external sampling assembly 6 can be configured to be a trace enrichment device. Here, the first sample loop 62 of the external sampling valve 24 is replaced with a trap column 80.

Figure 14A:
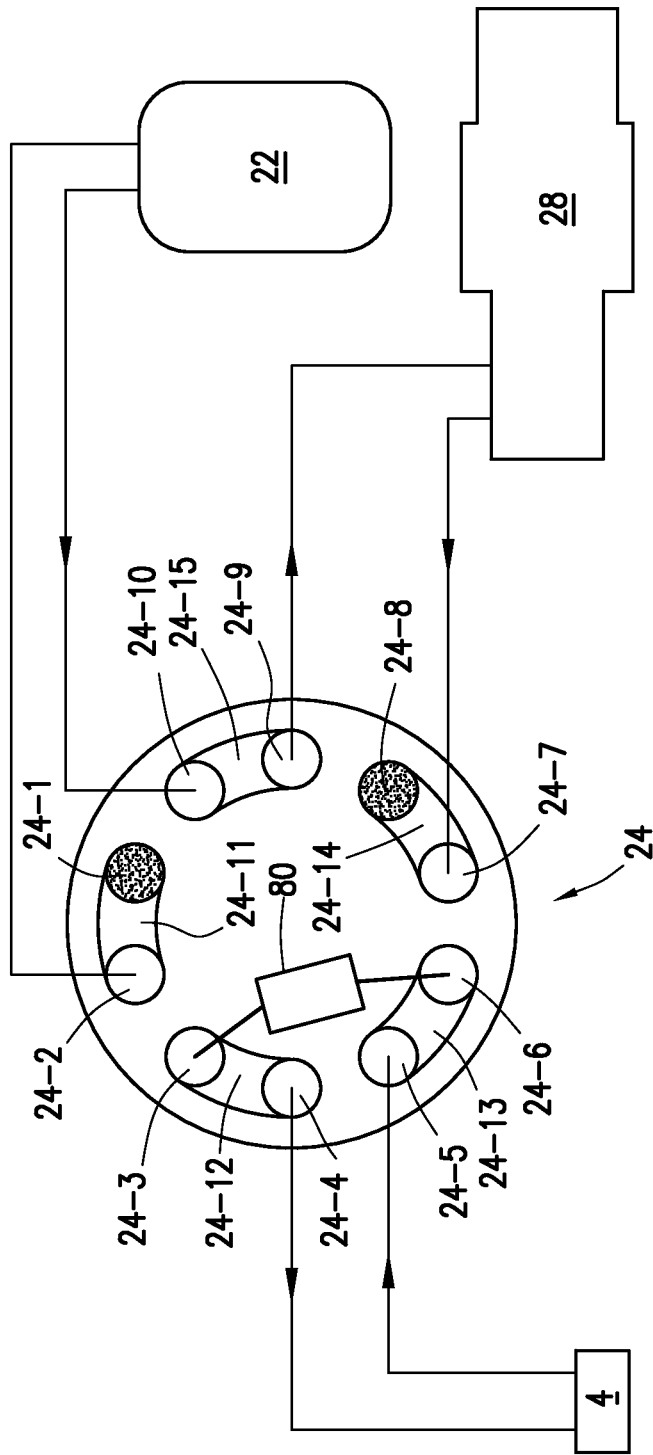
FIG. 14A shows the external sampling assembly configured to be a trace enrichment device where sample is drawn from the reactor into the external sampling valve having a trap column and sample is discharged to the process sample manager.
Figure 14B:
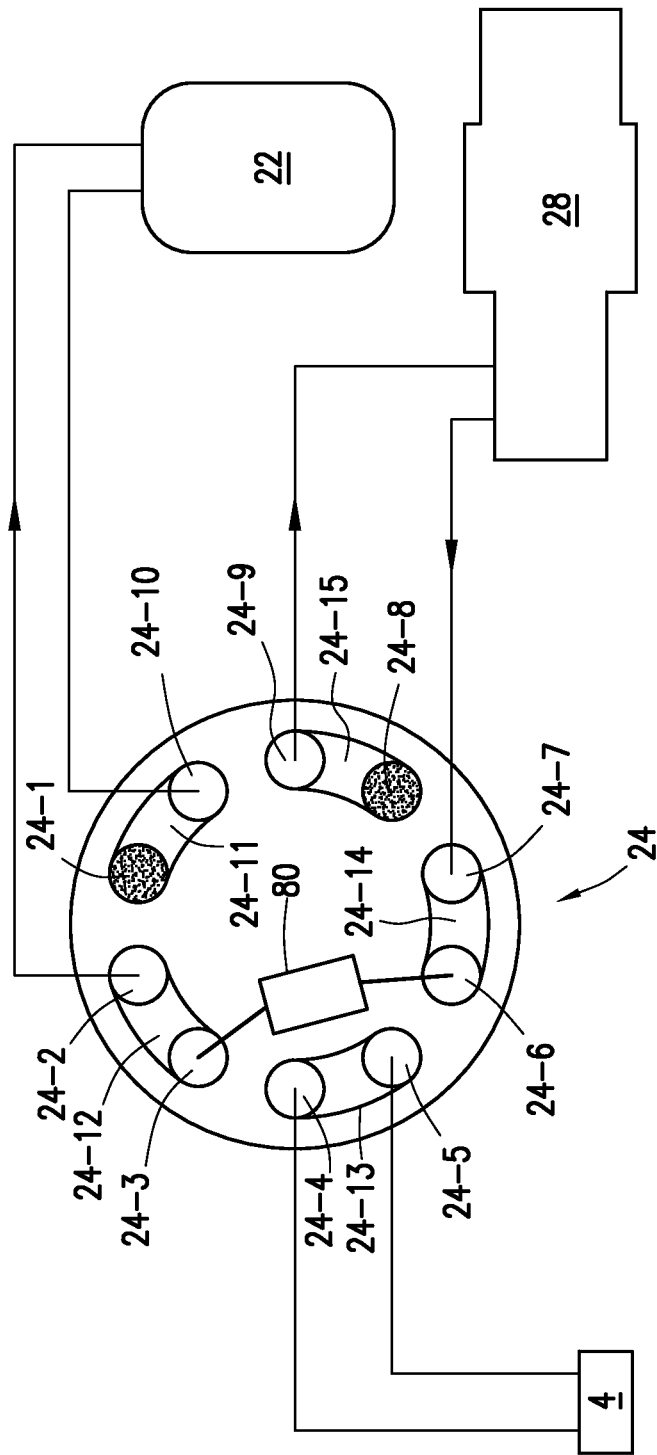
FIG. 14B shows the external sampling assembly configured to be a trace enrichment device where sample is loaded onto the trap column of the external sampling valve and recirculated back to the reactor.

As shown in FIGS. 14A and 14B and as noted above, the external sampling valve 24 has ten fluidic ports 24-1, 24-2, 24-3, 24-4, 24-5, 24-6, 24-7, 24-8, 24-9, and 24-10 and five flow-through conduits 24-11, 24-12, 24-13, 24-14, and 24-15. Fluidic ports 24-1 and 24-8 are plugged and are used to dead-end the connected tubes. The trap column 80 replaces the first sample loop 62 and is connected to fluidic ports 24-3 and 24-6.

As described above, the external sampling valve 24 toggles between two configurations, the first configuration and the second configuration as described herein and in three steps: draw sample, load sample and discharge sample. As shown in FIG. 14A, in the first configuration, sample is drawn from the reactor 22 flowing through fluidic port 24-10, fluidic conduit 24-15 and out fluidic port 24-9 of the external sampling valve 24 to the external pump 28. As shown in FIG. 14B, in the second configuration, the external sampling valve 24 rotates by one port position. In the second configuration, the external pump 28 discharges sample into fluidic port 24-7 through fluidic conduit 24-14 and fluidic port 24-6. Sample flows into and out of the trap column 80 into fluidic port 24-3 through fluidic conduit 24-12 and fluidic port 24-2 recirculating back to the reactor 22. As shown in FIG. 14B, the valve 24 is rotated clockwise and numbered accordingly. Yet, the external sampling valve 24 could rotate counterclockwise to achieve the same flow of sample. The external sampling valve 24 then rotates toggling back to the first configuration where purified sample is sent to the process sample manager 4.

The External Sampling Assembly: An On-line Injector

Figure 15A:
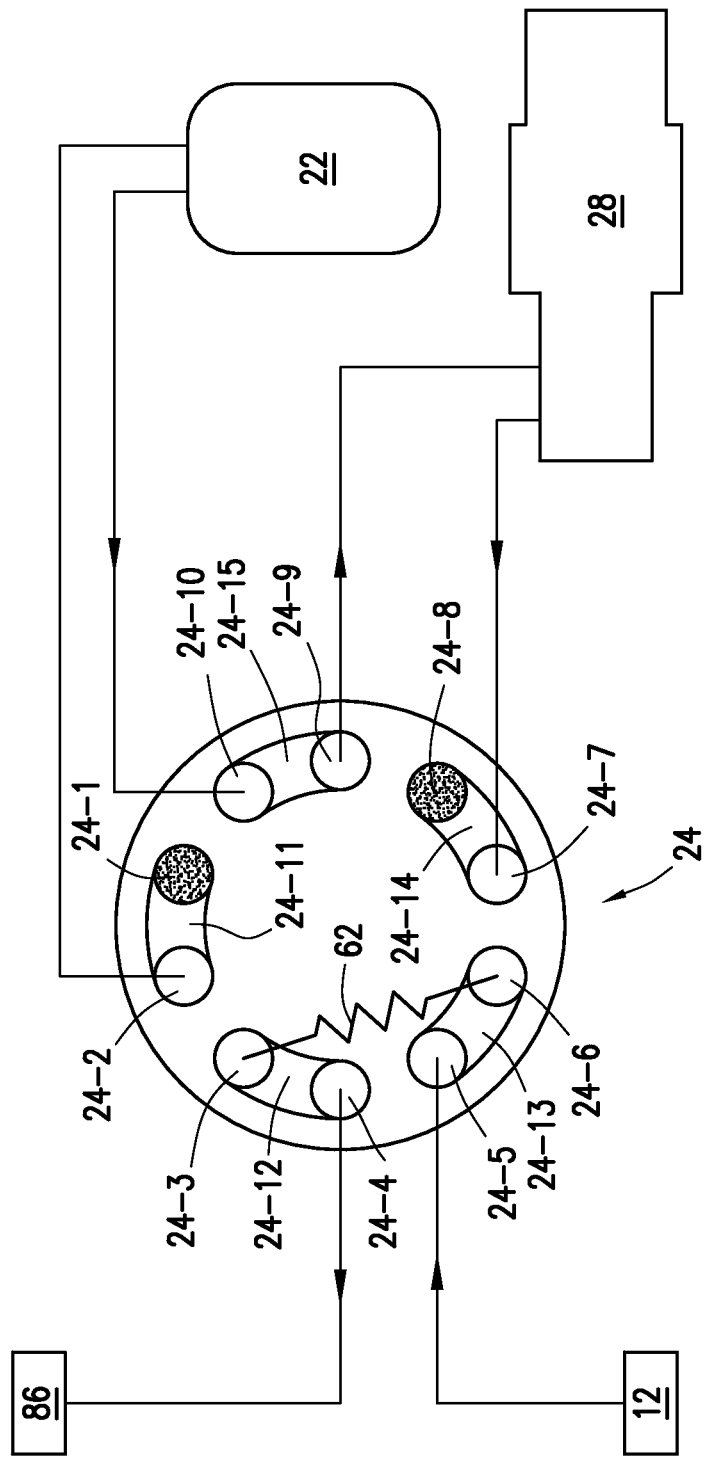
FIG. 15A shows the external sampling assembly configured to be an on-line injector, the external sampling assembly is connected to the solvent delivery system (via a volume pump) and fluidically connected to a column or detector.
Figure 15B:
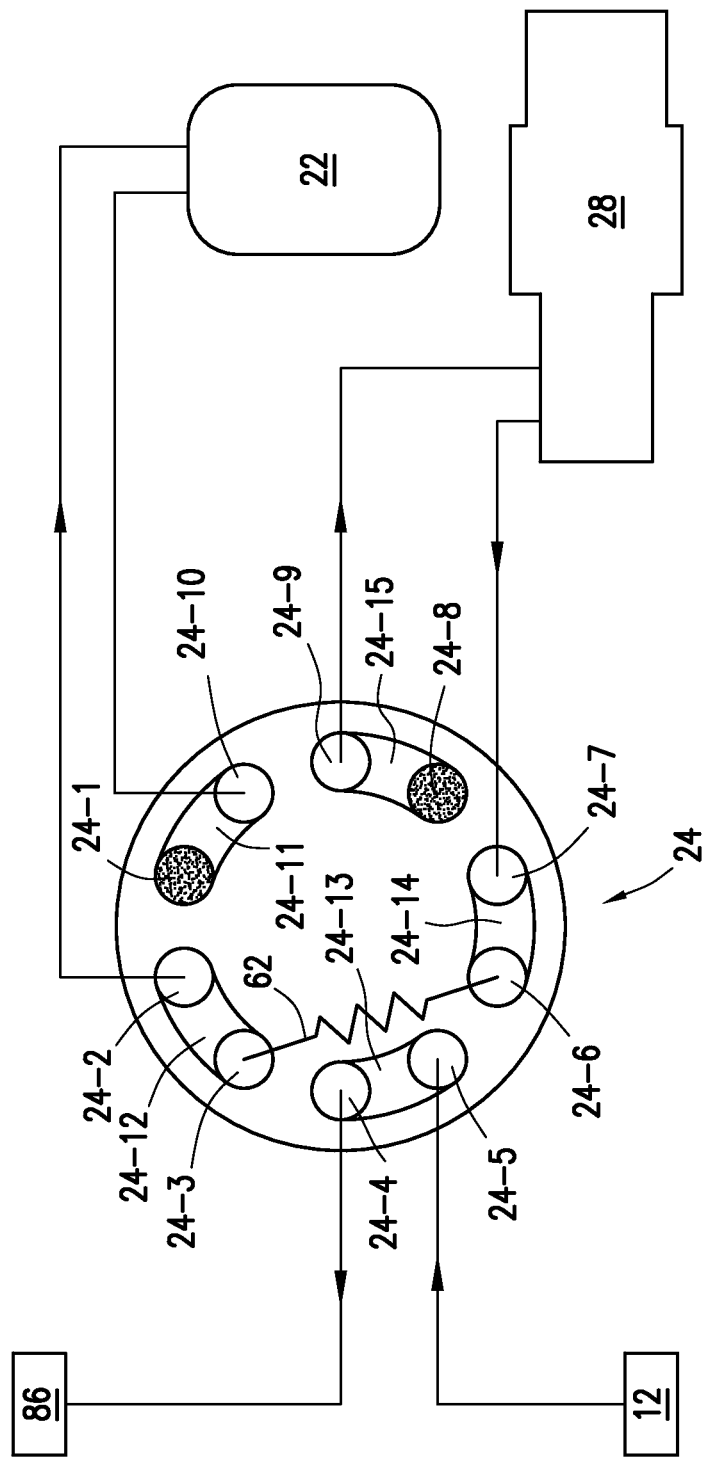
FIG. 15B shows the external sampling assembly configured as the on-line injector where sample is drawn through the sample loop and discharged to a composition stream fluidically connected to a column or detector.

The external sampling assembly 6 can be configured to be an on-line injector. As shown in FIGS. 15A and 15B, the external sampling valve 24 is connected to the solvent delivery system 12 and to the column 86 or detector (not shown). As noted herein, the external sampling valve 24 has ten fluidic ports 24-1, 24-2, 24-3, 24-4, 24-5, 24-6, 24-7, 24-8, 24-9, and 24-10 and five flow-through conduits 24-11, 24-12, 24-13, 24-14, and 24-15. Fluidic ports 24-1 and 24-8 are plugged and are used to dead-end the connected tubes. The first sample loop 62 is connected to fluidic ports 24-3 and 24-6. As shown in FIGS. 15A and 15B, the solvent delivery system 12 is connected to fluidic port 24-5 and fluidic port 24-4 is connected to the column 86.

As described above, the external sampling valve 24 toggles between two configurations, the first configuration and the second configuration as described herein and in three steps: draw sample, load sample and discharge sample. As shown in FIG. 15A, in the first configuration, sample is drawn from the reactor 22 flowing through fluidic port 24-10, fluidic conduit 24-15 and out fluidic port 24-9 of the external sampling 24 to the external pump 28. In addition, solvent is pumped from the solvent delivery system 12 to the external sampling valve 24 through fluidic port 24-5 into fluidic conduit 24-13 and out fluidic port 24-6 into the first sample loop 62 into fluidic port 24-3 through fluidic conduit 24-12 and out fluidic port 24-4 to the column 86.

As shown in FIG. 15B, in the second configuration, the external sampling valve 24 rotates by one port position. In the second configuration, the external pump 28 discharges sample into fluidic port 24-7 through fluidic conduit 24-14 and fluidic port 24-6. Sample flows into and out of the first sample loop 62 into fluidic port 24-3 through fluidic conduit 24-12 and fluidic port 24-2 recirculating back to the reactor 22. As shown in FIG. 15B, the external sampling valve 24 is rotated clockwise and numbered accordingly. Yet, the external sampling valve 24 could rotate counterclockwise to achieve the same flow of sample.

The external sampling valve 24 then rotates toggling back to the first configuration where the solvent is mixed with drawn sample in the external sampling valve 24 and sent to the column 86. Also, sample is drawn from the reactor 22 by the external pump 28 as described immediately above.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

I claim:

1. A sampling system configured to automatically acquire a sample from at least one non-pressurized source of the sample comprising: an external sampling assembly in fluidic communication with the at least one source of the sample, the external sampling assembly comprising an external sampling valve having a first sample loop and an external pump; and a process sample manager connected to the external sampling assembly, wherein the external sampling valve has a first configuration in which the external sampling valve is configured to place the process sample manager in fluidic communication with the first sample loop, and a second configuration in which the external sampling valve is configured to place the external pump in fluidic communication with the first sample loop.

2. The sampling system of claim 1, the process sample manager is in fluidic communication with a column or a detector.

3. The sampling system of claim 1, wherein the process sample manager comprises an online sampling valve connected to the external sampling valve.

4. The sampling system of claim 3, wherein in the first configuration, the first sample loop of the external sampling valve is in fluidic communication with the online sampling valve.

5. The sampling system of claim 4, the process sample manager further comprising a priming valve and a fluidic tee, wherein the priming valve is connected to the online sampling valve and the fluidic tee.

6. The sampling system of claim 5, wherein the process sample manager further comprises a diluent source and a diluent pump wherein the diluent pump and the diluent source are connected to the priming valve and the diluent pump is in fluidic communication with the diluent source or the fluidic tee.

7. The sampling system of claim 6, wherein the process pump is configured to be in fluidic communication with the external sampling assembly or the first wash reservoir.

8. The sampling system of claim 1, wherein the process sample manager further comprises a process valve connected to a first wash reservoir and a process pump.

9. A sampling system configured to acquire sample from a plurality of non-pressurized sources of sample for injection into a column or detector comprising:
an external sampling assembly having a plurality of external sampling valves, at least two selection valves and an external pump, wherein each said external sampling valve comprises a first sample loop, each said external sampling valve having a first configuration in which the external sampling valve is configured to place the source of sample in fluidic communication with the external pump and a second configuration in which the external sampling valve is configured to place the external pump in fluidic communication with the first sample loop.

10. The sampling of claim 9, wherein in the first configuration, the first sample loop is in fluidic communication with the at least two selection valves.

11. The sampling system of claim 10, wherein the process sample manager is in fluidic communication with a solvent delivery system.

12. The sampling system of claim 9, further comprising a process sample manager, wherein each of the at least two selection valves is connected to the process sample manager.

13. The sampling system of claim 12, the process sample manager further comprising an online sampling valve connected to each said selection valve.

14. The sampling system of claim 13 wherein the process sample manager further comprises a priming valve and fluidic tee, wherein the online sampling valve is in fluidic communication with the priming valve and the fluidic tee.

15. The sampling system of claim 9, wherein the process sample manager further comprises a process valve connected to the external sampling valve and the process valve is configured to discharge wash to the external sampling valve.

16. A sampling system configured to acquire sample from a plurality of non-pressurized sources of sample and discharge sample into a column or detector comprising:
an external sampling assembly having a plurality of external sampling valves, at least two selection valves, and an external pump, wherein each said external sampling valve has a first sample loop, a first configuration in which the external sampling valve is configured to place the source of sample in fluidic communication with the external pump and a second configuration in which the external sampling valve is configured to place the external pump in fluidic communication with the first sample loop; and
a process sample manager, wherein each of the at least two selection valves is connected to the process sample manager.

17. The sampling system of claim 16, wherein in the first configuration, the selection valve is in fluidic communication with the first sample loop.

18. The sampling system of claim 16, wherein the process sample manager comprises an online sampling valve connected to the at least two selection valves.

19. The sampling system of claim 18, wherein in the first configuration, the first sample loop is in fluidic communication with the on-line sampling valve.

20. The sampling system of claim 19, wherein the process sample manager is in fluidic communication with a solvent delivery system.

* * * * *